United States Patent
Hagiwara et al.

(10) Patent No.: US 8,846,966 B2
(45) Date of Patent: Sep. 30, 2014

(54) METHOD FOR PRODUCING ALKOXYCARBONYLFLUOROALKANE-SULFONIC ACID SALT

(75) Inventors: Yuji Hagiwara, Kawagoe (JP); Ryozo Takihana, Kawagoe (JP); Masanori Fushimi, Kawagoe (JP); Yoshimi Isono, Kawagoe (JP); Satoru Narizuka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 192 days.

(21) Appl. No.: 13/126,078

(22) PCT Filed: Oct. 21, 2009

(86) PCT No.: PCT/JP2009/068117
§ 371 (c)(1), (2), (4) Date: Apr. 26, 2011

(87) PCT Pub. No.: WO2010/050392
PCT Pub. Date: May 6, 2010

(65) Prior Publication Data
US 2011/0207954 A1    Aug. 25, 2011

(30) Foreign Application Priority Data

Oct. 29, 2008 (JP) .................. 2008-278198
Sep. 30, 2009 (JP) .................. 2009-225759

(51) Int. Cl.
| | | |
|---|---|---|
| C07C 211/05 | (2006.01) | |
| C07C 211/07 | (2006.01) | |
| C07C 211/63 | (2006.01) | |
| C07C 303/02 | (2006.01) | |
| C07C 303/22 | (2006.01) | |
| C07C 303/44 | (2006.01) | |
| C07C 313/04 | (2006.01) | |

(52) U.S. Cl.
CPC ............. *C07C 313/04* (2013.01); *C07C 211/63* (2013.01); *C07C 303/44* (2013.01); *C07C 211/07* (2013.01); *C07C 303/02* (2013.01); *C07C 211/05* (2013.01); *C07C 303/22* (2013.01)
USPC ........................................... 558/52

(58) Field of Classification Search
None
See application file for complete search history.

(56) References Cited

U.S. PATENT DOCUMENTS

| | | | |
|---|---|---|---|
| 2,852,554 A | 9/1958 | England et al. | |
| 7,414,148 B2 * | 8/2008 | Fujiwara et al. | ............. 562/100 |
| 2008/0108846 A1 | 5/2008 | Fujiwara et al. | |

FOREIGN PATENT DOCUMENTS

| | | |
|---|---|---|
| CA | 2049772 A1 | 2/1992 |
| JP | 4-230645 A | 8/1992 |
| JP | 2002-214774 A | 7/2002 |
| JP | 2004-4561 A | 1/2004 |
| JP | 2004-117959 A | 4/2004 |
| JP | 2005-84365 A | 3/2005 |
| JP | 2008-94835 A | 4/2008 |
| JP | 2008-133262 A | 6/2008 |

OTHER PUBLICATIONS

Liechti et al., caplus an1906:40834.*
International Search Report with partial English translation dated Dec. 8, 2009 (three (3) pages).
Form PCT/ISA/237 dated Dec. 9, 2009 (three (3) pages).

* cited by examiner

*Primary Examiner* — Sun Jae Yoo
(74) *Attorney, Agent, or Firm* — Crowell & Moring LLP

(57) ABSTRACT

In the present invention, a target alkoxycarbonylfluoroalkanesulfonic acid salt is obtained by using a halofluoroalkanoic acid ester as a starting raw material, sulfinating the halofluoroalkanoic acid ester in the presence of an amine (as a first step), and then, oxidizing the resulting sulfination product (as a second step). Further, an alkoxycarbonylfluoroalkanesulfinic acid onium salt, which is useful as a photoacid generator, is obtained by salt exchange reaction of the alkoxycarbonylfluoroalkanesulfonic acid salt.

6 Claims, No Drawings

METHOD FOR PRODUCING ALKOXYCARBONYLFLUOROALKANE-SULFONIC ACID SALT

TECHNICAL FIELD

The present invention relates to a method for producing an alkoxycarbonylfluoroalkanesulfonic acid salt, which is useful as a photoacid generator, or an intermediate thereof, of a chemically amplified resist material suitably applicable for fine processing, notably photolithography, in the manufacturing of semiconductor devices.

BACKGROUND ART

In recent years, there has been a rapid advance toward finer pattern rules for high integration and high speed performance of LSI devices. The application of shorter-wavelength exposure light sources is one factor behind the advance to the finer pattern rules. For example, the wavelength reduction from mercury-lamp i line (365 nm) to KrF excimer laser radiation (248 nm) enables mass production of 64-Mbit DRAM (Dynamic Random Access Memory) (with a processing size of 0.25 μm or smaller). Further, lithography process using ArF excimer laser radiation (193 nm) has been applied for production of DRAM with an integration of 256M and of 1 G or higher.

As resist materials suitable for exposure to such short-wavelength radiation, attention is being given to "chemically amplified resist materials". The chemically amplified resist material is a pattern forming material that contains a radiation-sensitive acid generator (hereinafter referred to as a "photoacid generator") capable of generating an acid by irradiation with energy radiation (hereinafter referred to as "exposure") and forms a resist pattern according to a photomask shape by causing a change in the developer solubility of exposed portions of the resist film through a reaction using the acid generated by exposure as a catalyst and thereby dissolving the exposed portions of the resist film.

Various researches are also being made on photoacid generators for use in chemically amplified resist materials. A conventional chemically amplified resist material for exposure to KrF excimer laser radiation uses a photoacid generator that generates an alkane- or arene-sulfonic acid. It is however known that, in the case of using such a photoacid generator in an ArF chemically amplified resist material, the acidity of the generated acid is not sufficient for cleavage of an acid labile group of the resist resin so that the resist material has no pattern resolution or low resist sensitivity unsuitable for device production.

For this reason, the ArF chemically amplified resist material generally uses a photoacid generator that generates a perfluoroalkanesulfonic acid of high acidity, such as perfluorooctanesulfonic acid. However, the perfluorooctanesulfonic acid known by its acronym "PFOS" and derivatives thereof have the problems concerning the stability (non-degradability) due to C—F bonds and the biological concentration and accumulation due to hydrophobic and lipophilic natures. The above-mentioned problems are being raised against perfluoroalkanesulfonic acids of 5 or more carbon atoms.

In order to cope with these PFOS-related problems, the development of partially fluorinated alkanesulfonic acids of lower fluorine substitution degree is being pursued. For example, there have been developed, as photoacid generators, alkoxycarbonylfluoromethanesulfonic acid onium salts such as triphenylsulfonium methoxycarbonyldifluoromethanesulfonate (Patent Document 1), (4-methylphenyl)diphenylsulfonyl t-butoxycarbonyldifluoromethanesulfonate (Patent Document 2) and triphenylsulfonium (adamantane-1-ylmethyl)oxycarbonyldifluoromethanesulfonate (Patent Document 3).

Conventionally, a reaction mechanism of the following reaction formula [1] is known as a synthesis process of an alkoxycarbonylfluoromethanesulfonic acid onium salt.

[Chem. 1]

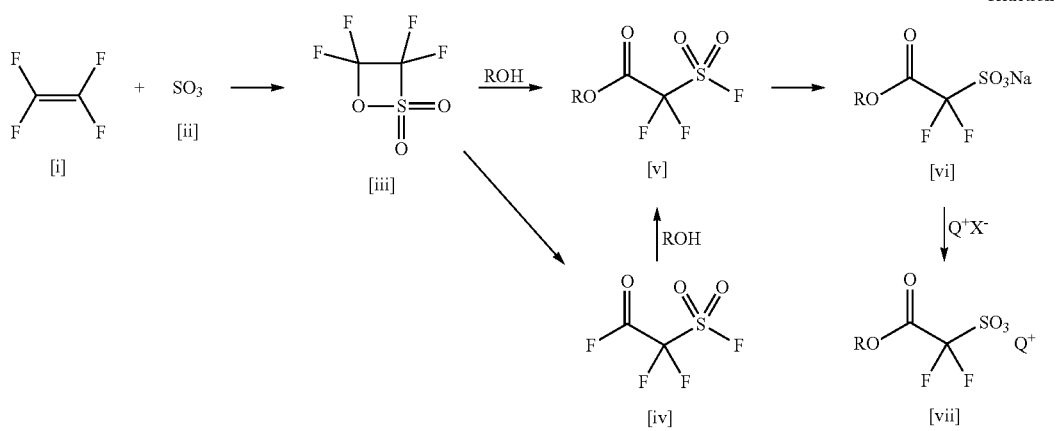

Reaction formula [1]

This reaction mechanism goes through synthesis of 3,3,4,4-tetrafluoro-[1,2]oxathietane-2,2-dioxide [iii] from tetrafluoroethylene [i] and sulfur trioxide [ii], synthesis of an acid fluoride [v] by ring-opening reaction of the dioxide [iii] with an alcohol (ROH), or by ring-opening isomerization of the dioxide [iii] to an acid fluoride [iv] followed by esterification of the acid fluoride [iv] with an alcohol (ROH), conversion of the acid fluoride [v], with the use of a basic metal salt (typically, sodium hydroxide), to a sulfonic acid salt (sulfonic acid sodium salt) [vi], and then, formation of the target alkoxycarbonyldifluoroalkanesulfonic acid onium salt by onium salt exchange reaction of the sulfonic acid salt [vi] with a sulfonic acid onium salt ($Q^+X^-$ where Q is a monovalent onium cation; and X is typically a halogen) (see Patent Documents 1 and 4).

There is also disclosed a process for hydrolyzing an acid fluoride [v] of the above reaction formula [1] with an amine/water system to thereby form a sulfonic acid ammonium salt (see Patent Document 5).

On the other hand, the present applicant has disclosed a production process of an alkoxycarbonylfluoromethanesulfonic acid onium salt as represented by the following reaction formula [2].

[Chem. 2]

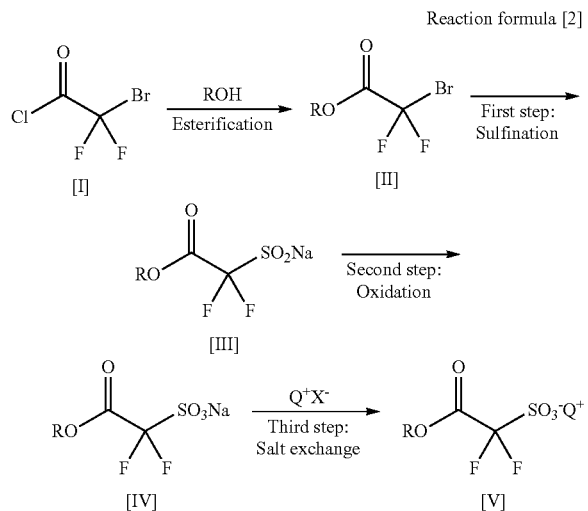

Reaction formula [2]

This process goes through synthesis of a halodifluoroacetic acid ester such as bromodifluoroacetic acid ester [II] by esterification of a halodifluoroacetic acid halide e.g. bromodifluoroacetic acid chloride [I], a halodifluoroacetic acid salt or a halodifluoroacetic acid anhydride, sulfination of the halodifluoroacetic acid to a sulfinic acid salt such as alkoxycarbonyldifluoromethanesulfinic acid sodium salt [III], oxidation of the sulfinic acid salt to a sulfonic acid salt such as alkoxycarbonyldifluoromethanesulfonic acid sodium salt [IV], and then, formation of the target alkoxycarbonyldifluoroalkanesulfonic acid onium salt as an acid generator compound by onium salt exchange reaction of the sulfonic acid salt with a sulfonic acid onium salt ($Q^+X^-$ where Q is a monovalent onium cation; and X is typically a halogen) (see Patent Documents 6 and 7).

PRIOR ART DOCUMENTS

Patent Documents

Patent Document 1: Japanese Laid-Open Patent Publication No. 2004-117959

Patent Document 2: Japanese Laid-Open Patent Publication No. 2002-214774

Patent Document 3: Japanese Laid-Open Patent Publication No. 2004-004561

Patent Document 4: U.S. Pat. No. 2,852,554

Patent Document 5: Japanese Laid-Open Patent Publication No. 2008-094835

Patent Document 6: U.S. Pat. No. 7,414,148

Patent Document 7: Japanese Laid-Open Patent Publication No. 2008-133262

SUMMARY OF THE INVENTION

Problems to be Solved by the Invention

The production processes of Patent Documents 1 and 4 uses, as a raw material, 3,3,4,4-tetrafluoro-[1,2]oxathietane-2,2-dioxide [iii] synthesized from tetrafluoroethylene [i] and sulfur trioxide [ii]. This synthesis reaction is industrially difficult as it is necessary in the reaction to give sufficient consideration for safety due to the use of the explosive reagent. The thus-obtained 3,3,4,4-tetrafluoro-[1,2]oxathietane-2,2-dioxide [iii] is inevitably expensive. Thus, there is some hesitation in the industrial application of the process using such an expensive raw material. Further, a large amount of hydrogen fluoride or fluoride salt occurs as a by-product of the conversion reaction of the acid fluoride [iv] or [v]. It is know that, in the case of using a glass reactor, a fluorine ion liberated from hydrogen fluoride or fluoride salt causes corrosion and devitrification of the glass reactor. It is also impossible to use a metal reactor of iron, stainless steel etc. in the presence of not only a strong acid hydrogen fluoride itself, but also a fluoride salt as the fluoride salt generates hydrogen fluoride upon contact with an acid. There are thus various limitations to the material of the reactor used due to the occurrence of such a by-product.

The production processes of Patent Documents 6 and 7 disclosed by the present application enable easy, high-purity production of the alkoxycarbonylfluoroalkanesulfonic acid salt without the occurrence of hydrogen fluoride or fluoride salt as a by-product and thereby without limitations on the material of the reactor used. However, these processes mainly utilize alkoxycarbonyldifluoromethanesulfonic acid sodium salt as a raw material in the onium salt exchange reaction of the final process step. Although the alkoxycarbonyldifluoromethanesulfonic acid sodium salt can be converted to the target alkoxycarbonyldifluoroalkanesulfonic acid onium salt by the onium salt exchange reaction, an equivalent amount of (mainly) sodium halide simultaneously occurs as a by-product of the onium salt exchange reaction. The contamination of a metal content such as sodium into a chemically amplified resist material is strictly limited. In general, the allowable value of the metal content in the chemically amplified resist material is several hundred ppb or less (in some cases, several tens ppb or less). It is thus necessary in these processes to reduce the content of sodium derived from the sodium halide by-product to several hundred ppb or less, which results in a large process load.

As mentioned above, the conventional production processes of alkoxycarbonylfluoroalkanesulfonic acid salts have some problems. There has been a demand to establish an industrial production process of alkoxycarbonylfluoroalkanesulfonic acid salts which is efficiently applicable for a long time to come.

Means for Solving the Problems

In view of the foregoing, it is an object of the present invention to provide a production method suitable for industrial production of an alkoxycarbonylfluoroalkanesulfonic acid ammonium salt or onium salt and to provide a novel intermediate compound useful for this production method.

The present inventors have made extensive researches and consequently found a production method of an alkoxycarbonylfluoroalkanesulfonic acid salt, characterized in that: there is no particular limitation on the material of a reactor used as either hydrogen fluoride or fluoride salt does not occur as a by-product; and the operation of removal of a metal content such as sodium is simple so that the alkoxycarbonylfluoroalkanesulfonic acid salt can be obtained with high purity.

Namely, the present invention includes the following aspects.

[Inventive Aspect 1] A method for producing an alkoxycarbonylfluoroalkanesulfonic acid ammonium salt of the following general formula [1], comprising the following two steps:

a first step of reacting a halofluoroalkanoic acid ester of the following general formula [2] with a sulfinating agent in the presence of an amine or an ammonium salt to forming an alkoxycarbonylfluoroalkanesulfinic acid ammonium salt of the following general formula [3]; and a second step of reacting the alkoxycarbonylfluoroalkanesulfinic acid ammonium salt of the general formula [3] with an oxidizing agent, thereby obtaining the alkoxycarbonylfluoroalkanesulfonic acid ammonium salt of the general formula [1]

[Chem. 3]

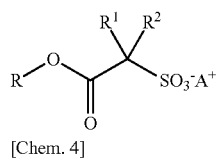

[1]

[Chem. 4]

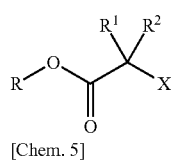

[2]

[Chem. 5]

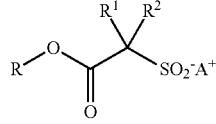

[3]

(wherein, in the general formula [1], R represents a $C_1$-$C_{10}$ straight or branched alkyl group, a $C_1$-$C_{10}$ straight or branched alkenyl group having at least at an end thereof a polymerizable double bond, a $C_3$-$C_{20}$ alicyclic organic group, an organic group formed of a $C_3$-$C_{20}$ alicyclic organic group and a straight alkylene group, a $C_3$-$C_{30}$ monocyclic or polycyclic lactone group, or a $C_6$-$C_{20}$ aryl group; a part or all of hydrogen atoms of the alkyl group, the alkenyl group, the alicyclic organic group, the organic group formed of the alicyclic organic group and the straight alkylene group, the monocyclic or polycyclic lactone group and the aryl group may be substituted with a fluorine atom, a hydroxyl group, a hydroxycarbonyl group or a $C_1$-$C_6$ straight, branched or cyclic alkoxy group; two hydrogen atoms on the same carbon atom of the alkyl group, the alkenyl group, the alicyclic organic group or the organic group formed of the alicyclic organic group and the straight alkylene group may be replaced with a single oxygen atom to form a keto group; and one of hydrogen atoms of the alkyl group may be substituted with a 2-acryloyloxy group, 2-methacryloyloxy group or 2-trifluoromethacryloyloxy group; $R^1$ and $R^2$ each independently represent a fluorine atom or a $C_1$-$C_6$ straight, branched or cyclic perfluoroalkyl group; and $A^+$ represents an ammonium ion; wherein, in the general formula [2], X represents a chlorine atom, a bromine atom or an iodine atom; and R, $R^1$ and $R^2$ have the same definitions as in the general formula [1]; and wherein, in the general formula [3], R, $R^1$, $R^2$ and $A^+$ have the same definitions as in the general formula [1]).

[Inventive Aspect 2] A method for producing an alkoxycarbonylfluoroalkanesulfonic acid onium salt of the following general formula [4], comprising the following three steps:

a first step of reacting a halofluoroalkanoic acid ester of the above general formula [2] with a sulfinating agent in the presence of an amine or an ammonium salt to form an alkoxycarbonylfluoroalkanesulfinic acid ammonium salt of the above general formula [3];

a second step of reacting the alkoxycarbonylfluoroalkanesulfinic acid ammonium salt of the general formula [3] with an oxidizing agent to form an alkoxycarbonylfluoroalkanesulfonic acid ammonium salt of the above general formula [1]; and a third step of performing salt exchange reaction of the alkoxycarbonylfluoroalkanesulfonic acid ammonium salt of the general formula [1] with a monovalent onium salt of the following general formula [5], thereby obtaining the alkoxycarbonylfluoroalkanesulfonic acid onium salt of the general formula [4]

[Chem. 6]

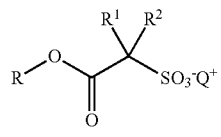

[4]

[Chem. 7]

$Q^+X'^-$

[5]

(wherein, in the general formula [4], R, $R^1$ and $R^2$ have the same definitions as in the general formula [1]; and $Q^+$ represents a sulfonium cation of the following general formula (a) or the following general formula (b) or an iodonium cation of the following general formula (c); and wherein, in the general formula [5], X' represents a monovalent anion)

[Chem. 8]

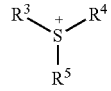

(a)

(wherein, in the general formula (a), $R^3$, $R^4$ and $R^5$ each independently represent a substituted or unsubstituted $C_1$-$C_{10}$ straight or branched alkyl, alkenyl or oxoalkyl group, or a substituted or unsubstituted $C_6$-$C_{18}$ aryl, aralkyl or aryloxoalkyl group; and two or more of $R^3$, $R^4$ and $R^5$ may be bonded to each other to form a ring with a sulfur atom in the formula)

[Chem. 9]

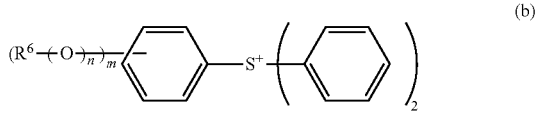
(b)

(wherein, in the general formula (b), $R^6$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; and n represents 0 or 1)

[Chem. 10]

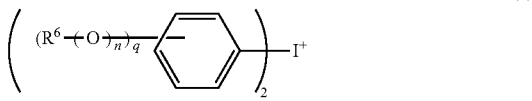
(c)

(wherein, in the general formula (c), $R^6$ represents a substituted or unsubstituted $C_1$-$C_{20}$ straight, branched or cyclic alkyl or alkenyl group, or a substituted or unsubstituted $C_6$-$C_{14}$ aryl group; q represents an integer of 0 to 5; and n represents 0 or 1).

[Inventive Aspect 3] The method according to Inventive Aspect 1 or 2, wherein $A^+$ represents an ammonium of the following general formula [6]

[Chem. 11]

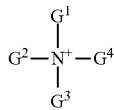
[6]

(wherein, in the general formula [6], $G^1$, $G^2$, $G^3$ and $G^4$ each independently represent a hydrogen atom, a $C_1$-$C_6$ alkyl group, a $C_1$-$C_6$ alkoxyalkyl group, a $C_3$-$C_{12}$ cycloalkyl group, a phenyl group which may be substituted, a $C_7$-$C_{12}$ aralkyl group which may be substituted, a naphthyl group which may be substituted, or a $C_5$-$C_{10}$ hetero aromatic group which may be substituted; and at least two or more of $G^1$, $G^2$, $G^3$ and $G^4$ may form a ring containing a hetero atom).

[Inventive Aspect 4] The method according to any one of Inventive Aspects 1 to 3, further comprising: purifying the alkoxycarbonylfluoroalkanesulfinic acid ammonium salt so as to reduce a metal content in the alkoxycarbonylfluoroalkanesulfinic acid ammonium salt by extracting with an organic solvent a crude product of the alkoxycarbonylfluoroalkanesulfinic acid ammonium salt obtained after the sulfination reaction of the first step, and then, washing a layer of the organic solvent with water.

[Inventive Aspect 5] The method according to any one of Inventive Aspects 1 to 4, further comprising: purifying the alkoxycarbonylfluoroalkanesulfinic acid ammonium salt by extracting with an organic solvent a crude product of the alkoxycarbonylfluoroalkanesulfinic acid ammonium salt obtained after the sulfination reaction of the first step, and then, washing a layer of the organic solvent with either an aqueous metal thiosulfate solution or an aqueous metal sulfite solution.

[Inventive Aspect 6] The method according to any one of Inventive Aspects 1 to 5, further comprising: purifying the alkoxycarbonylfluoroalkanesulfonic acid ammonium salt so as to reduce a metal content in the alkoxycarbonylfluoroalkanesulfonic acid ammonium salt by extracting with an organic solvent a crude product of the alkoxycarbonylfluoroalkanesulfonic acid ammonium salt obtained after the oxidation reaction of the second step, and then, washing a layer of the organic solvent with water.

[Inventive Aspect 7] A salt of the general formula [3]:

[Chem. 12]

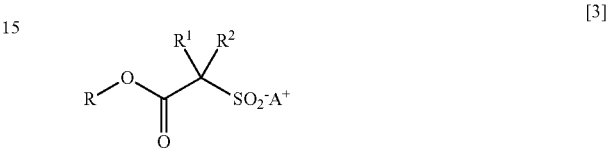
[3]

(wherein, in the general formula [3], R, $R^1$, $R^2$ and $A^+$ have the same definitions as in the general formula [1].

[Inventive Aspect 8] A salt of the general formula [7]:

[Chem. 13]

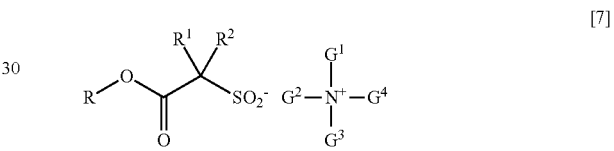
[7]

(wherein, in the general [7], R, $R^1$ and $R^2$ have the same definitions as in the general formula [1]; and $G^1$, $G^2$, $G^3$ and $G^4$ have the same definitions as in the general formula [6]).

[Inventive Aspect 9] (Adamantane-1-ylmethyl)oxycarbonyldifluoromethanesulfinic acid triethylammonium salt.

[Inventive Aspect 10] (Adamantane-1-ylmethyl)oxycarbonyldifluoromethanesulfinic acid tert-butylammonium salt.

The present invention has the advantages that: the raw reaction materials are low-priced; the reaction operations are simple; and there are no particular limitations on the reactor used. The present invention also has the advantage that the target compound can be obtained with high purity by the above purification operation.

BEST MODES FOR CARRYING OUT THE INVENTION

The present invention will be described in detail below.

The present invention provides a reaction process that essentially goes through the steps of: reacting a halofluoroalkanoic acid ester of the general formula [2] with a sulfinating agent in the presence of an amine or ammonium salt to form a alkoxycarbonylfluoroalkanesulfinic acid ammonium salt of the general formula [3] (first step: sulfination reaction); and then, reacting the alkoxycarbonylfluoroalkanesulfinic acid ammonium salt of the general formula [3] with an oxidizing agent, thereby obtaining an alkoxycarbonylfluoroalkanesulfonic acid ammonium salt of the general formula [1] (second step: oxidation reaction) as indicated in the reaction formula [3]. The reaction process of the present invention may further go through the step of reacting the alkoxycarbonylfluoroalkanesulfonic acid ammonium salt of the general formula [1] with a monovalent onium salt of the general formula [5] to thereby obtain an alkoxycarbonylfluoroalkanesulfonic acid onium salt of the general formula [4] (third step: salt exchange reaction).

[Chem. 14]

Reaction formula [3]

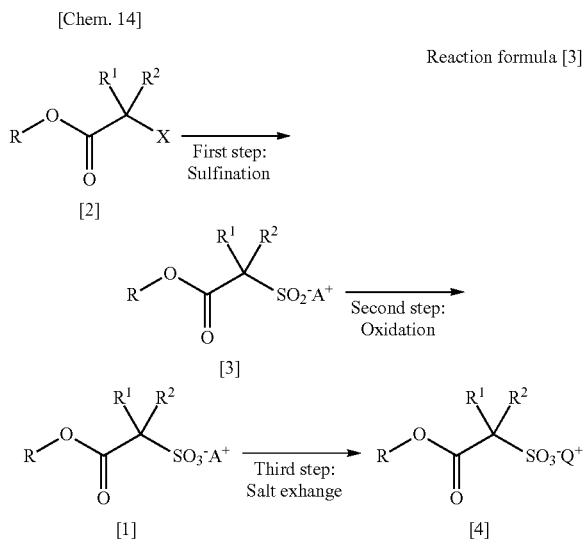

Each of the reaction steps will be explained in detail below.
[First Step: Sulfination Reaction]

In the first step (sulfination reaction step), the halofluoroalkanoic acid ester of the general formula [2] is reacted with the sulfinating agent in the presence of the amine or ammonium salt to form the alkoxycarbonylfluoroalkanesulfinic acid ammonium salt of the general formula [3].

[Chem. 15]

[Chem. 16]

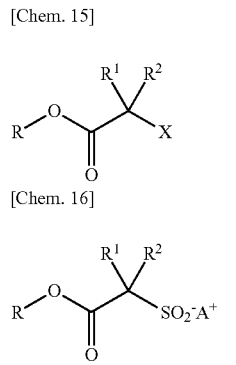

In the general formula [2], X represents a chlorine atom, a bromine atom or an iodine atom. In the general formula [3], $A^+$ represents an ammonium ion.

In the general formulas [2] and [3], $R^1$ and $R^2$ each independently represent a fluorine atom or a $C_1$-$C_6$ straight, branched or cyclic perfluoroalkyl group. Further, R represents a $C_1$-$C_{10}$ straight or branched alkyl group, a $C_1$-$C_{10}$ straight or branched alkenyl group having at least at an end thereof a polymerizable double bond, a $C_3$-$C_{20}$ alicyclic organic group, an organic group formed of a $C_3$-$C_{20}$ alicyclic organic group and a straight alkylene group, a $C_3$-$C_{30}$ monocyclic or polycyclic lactone group, or a $C_6$-$C_{20}$ aryl group; a part or all of hydrogen atoms of the alkyl group, the alkenyl group, the alicyclic organic group, the organic group formed of the alicyclic organic group and the straight alkylene group, the monocyclic or polycyclic lactone group and the aryl group may be substituted with a fluorine atom, a hydroxyl group, a hydroxycarbonyl group or a $C_1$-$C_6$ straight, branched or cyclic alkoxy group; two hydrogen atoms on the same carbon atom of the alkyl group, the alkenyl group, the alicyclic organic group or the organic group formed of the alicyclic organic group and the straight alkylene group may be replaced with a single oxygen atom to form a keto group; and one of hydrogen atoms of the alkyl group may be substituted with a 2-acryloyloxy group, 2-methacryloyloxy group or 2-trifluoromethacryloyloxy group.

Examples of the skeleton (the structure part other than the ester moiety) of the halofluoroalkanoic acid ester are chlorodifluoroacetic acid ester, bromodifluoroacetic acid ester, iododifluoroacetic acid ester, 2-chloro-2,3,3,3-tetrafluoropropanoic acid ester, 2-bromo-2,3,3,3-tetrafluoropropanoic acid ester, 2-iodo-2,3,3,3-tetrafluoropropanoic acid ester, 2-chloro-2-(trifluoromethyl)-3,3,3-trifluoropropanoic acid ester, 2-bromo-2-(trifluoromethyl)-3,3,3-trifluoropropanioic acid ester and 2-iodo-2-(trifluoromethyl)-3,3,3-trifluoropropanic acid ester. Among others, chlorodifluoroacetic acid ester, bromodifluoroacetic acid ester, 2-chloro-2,3,3,3-tetrafluoropropanoic acid ester and 2-bromo-2,3,3,3-tetrafluoropropanoic acid ester are preferred in view of ease of availability and low cost. In view of reactivity in addition to ease of availability and low cost, bromodifluoroacetic acid ester and 2-bromo-2,3,3,3-tetrafluoropropanoic acid ester are particularly preferred.

Examples of the $C_1$-$C_{10}$ straight or branched alkyl group are methyl, ethyl, n-propyl, i-propyl, n-butyl, t-butyl, n-pentyl, n-hexyl, n-heptyl, n-octyl, n-nonyl and n-decyl.

Examples of the $C_1$-$C_{10}$ alkenyl group having the polymerizable double bond at least at the end thereof are vinyl, 1-methylethenyl, allyl, 3-butenyl, 1-methylallyl, 2-methylallyl, 4-pentenyl and 5-hexenyl.

Examples of the $C_3$-$C_{20}$ alicyclic organic group are cyclopentyl, cyclohexyl, adamantyl, norbornyl, camphoroyl, cyclopentylmethyl, cyclopentylethyl, cyclohexylmethyl, cyclohexylethyl, adamantylmethyl, adamantylethyl, norbornylmethyl, norbornylethyl, camphoroylmethyl and camphoroylethyl.

The organic group formed of the $C_3$-$C_{20}$ alicyclic organic group and the straight alkylene group refers to an organic group in which the alicyclic organic group and the straight alkylene group are joined by a monovalent bond. Examples of such an organic group are cyclopropylmethyl, cyclobutylmethyl, cyclopentylmethyl, cyclohexylmethyl, bornylmethyl, norbornylmethyl and adamantylmethyl.

Examples of the $C_3$-$C_{30}$ monocyclic or polycyclic lactone group are γ-butyrolactone, γ-valerolactone, angelicalactone, γ-hexylactone, γ-heptalactone, γ-octalactone, γ-nonalactone, 3-methyl-4-octanolide (whisky lactone), γ-decalactone, γ-undecalactone, γ-dodecalactone, jasmolactone (7-decenolactone), δ-hexylactone, 4,6,6(4,4,6)-trimethyltetrahyropyrane-2-one, δ-octalactone, δ-nonalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyl lactone, jasmine lactone, cis-jasmone lactone, methyl-γ-decalactone and groups of the following structures.

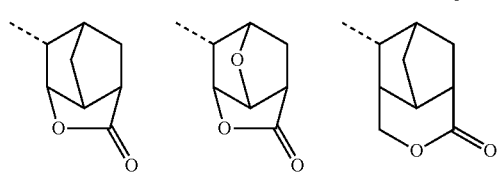

(The dotted line indicates the bonding position.)

Examples of the $C_6$-$C_{20}$ aryl group are phenyl, o-tolyl, m-tolyl, p-tolyl, p-hydroxyphenyl, 1-naphtyl, 1-anthracenyl and benzyl.

As mentioned above, a part or all of hydrogen atoms of the alkyl group, the alkenyl group, the alicyclic organic group, the organic group formed of the alicyclic organic group and the straight alkylene group, the monocyclic or polycyclic lactone group and the aryl group may be substituted with a fluorine atom, a hydroxyl group, a hydroxycarbonyl group or a $C_1$-$C_6$ straight, branched or cyclic alkoxy group. Two hydrogen atoms on the same carbon atom of the alkyl group, the alkenyl group, the alicyclic organic group or the organic group formed of the alicyclic organic group and the straight alkylene group may be replaced with a single oxygen atom to form a keto group. Further, one of hydrogen atoms of the alkyl group may be substituted with a 2-acryloyloxy group, 2-methacryloyloxy group or 2-trifluoromethacryloyloxy group.

As the sulfinating agent, there can be used those of the general formula [8].

[Chem. 18]

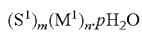 [8]

In the general formula [8], $S^1$ represents $S_2O_4$, $HOCH_2SO_2$, $SO_4$ or $HSO_4$; m and n each represent an integer; p represents 0 (zero) or an integer; and $M^1$ represents Li, Na, K or $NH_4$.

Specific examples of the sulfinating agent are lithium dithionite, sodium dithionite, potassium dithionite, ammonium dithionite, lithium hydroxymethanesulfinate, sodium hydroxymethanesulfinate, potassium hydroxymethanesulfinate, ammonium hydroxymethanesulfinate, lithium sulfite, sodium sulfite, potassium sulfite, ammonium sulfite, lithium bisulfite, sodium bisulfite, potassium bisulfite and ammonium bisulfite. Among others, sodium dithionite and potassium dithionite are preferred. Particularly preferred is sodium dithionite.

The mole ratio of the sulfinating agent used relative to the halofluoroalkanoic acid ester [2] is generally in the range of 0.5 to 10, preferably 0.9 to 5.0, more preferably 1.0 to 2.0.

In general, a sulfination reaction using a sulfinating agent is performed with the addition of a base in view of the fact that the sulfination reaction proceeds even without the addition of the base but can be promoted with the addition of the base. Typical examples of the base added in the sulfination reaction are inorganic bases such as sodium carbonate, potassium carbonate, sodium hydrogencarbonate and potassium hydrogencarbonate. By contrast, the present invention is remarkably characterized in that the sulfination reaction is performed with the use of an amine or an ammonium salt as the base.

The amine used (coexisting) in this sulfination reaction step is preferably a free amine that occurs upon removal of a proton ($H^+$) from an ammonium ion of the general formula [6] where at least one of $G^1$, $G^2$, $G^3$ and $G^4$ is a hydrogen atom.

[Chem. 19]

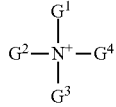 [6]

In the general formula [6], $G^1$, $G^2$, $G^3$ and $G^4$ each independently represent a hydrogen atom, a $C_1$-$C_6$ alkyl group, a $C_1$-$C_6$ alkoxyalkyl group, a $C_3$-$C_{12}$ cycloalkyl group, a phenyl group which may be substituted, a $C_7$-$C_{12}$ aralkyl group which may be substituted, a naphtyl group which may be substituted, or a $C_5$-$C_{10}$ hetero aromatic group which may be substituted; and at least two or more of $G^1$, $G^2$, $G^3$ and $G^4$ may form a ring containing a hetero atom.

Specific examples of the amine are ammonia, methylamine, dimethylamine, trimethylamine, ethylamine, diethylamine, triethylamine, n-propylamine, di-n-propylamine, tri-n-propylamine, i-propylamine, di-i-propylamine, tri-i-propylamine, n-butylamine, di-n-butylamine, tri-n-butylamine, sec-butylamine, di-sec-butylamine, tri-sec-butylamine, tert-butylamine, di-tert-butylamine, tri-tert-butylamine, diisopropylethylamine, phenylamine, diphenylamine, triphenylamine, benzylamine, benzylmethylamine, benzyldimethylamine, benzylethylamine, benzyldiethylamine, 2-methylbenzylamine, 3-methylbenzylamine, 4-methylbenzylamine and organic bases of the following structures.

[Chem. 20]

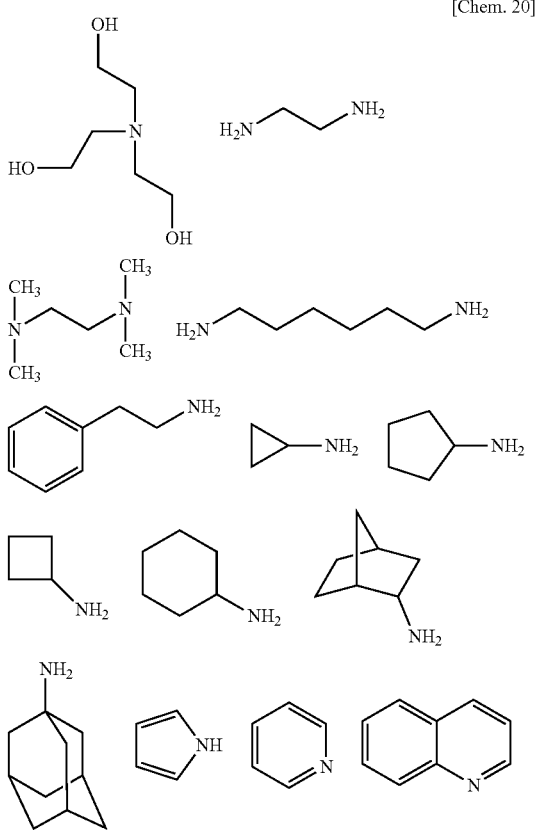

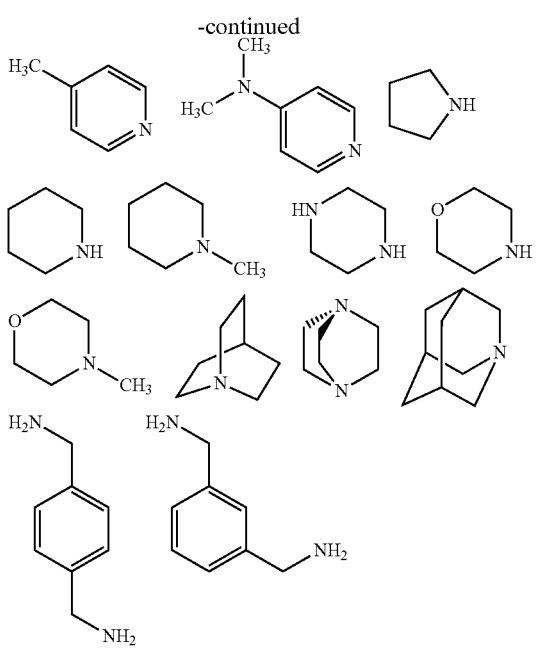

Among others, preferred are trimethylamine, triethylamine, tri-n-propylamine, tri-i-propylamine, tri-n-butylamine, tri-sec-butylamine, tri-tert-butylamine, diisopropylethylamine, triphenylamine, tert-butylamine, benzylamine, benzylmethylamine, benzyldimethylamine, benzylethylamine, benzyldiethylamine, 2-methylbenzylamine, 3-methylbenzylamine, 4-methylbenzylamine and organic bases of the following structures.

[Chem. 21]

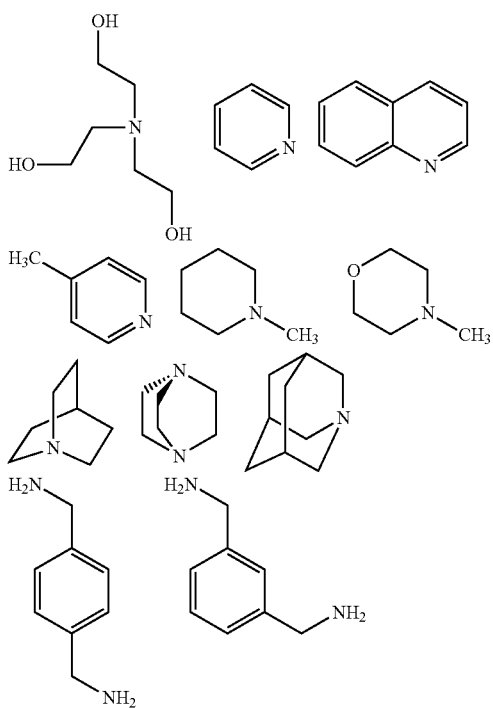

Particularly preferred are trimethylamine, triethylamine, diisopropylethylamine, tert-butylamine and benzylamine not only for ease of availability but also for noticeable improvement in the reactivity of the sulfination reaction and sufficient improvement in the lipid solubility of the resulting alkoxycarbonylfluoroalkanesulfinic acid ammonium salt.

The mole ratio of the amine used relative to the halofluoroalkanoic acid ester [2] is generally in the range of 1.0 to 10.0, preferably 1.1 to 2.0. If the mole ratio of the amine is less than 1.0, there occurs as a by-product alkoxycarbonylfluoroalkanesulfinic acid metal salt etc. due to the presence of a cation (a metal cation such as sodium ion, potassium ion or lithium ion) derived from the sulfinating agent. In this case, it becomes unfavorably difficult to separate the ammonium salt from the metal salt by the subsequent post-treatment operation. Further, the yield of the target compound becomes unfavorably deteriorated. There is no problem if the mole ratio of the amine exceeds 10.0. It is however economically disadvantageous and unfavorable to use such a large amount of amine.

The ammonium salt used (coexisting) in this sulfination reaction step is preferably an ammonium salt the general formula [9].

[Chem. 22]

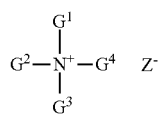

[9]

In the general formula [9], $G^1$, $G^2$, $G^3$ and $G^4$ have the same definitions as in the general formula [6]; and $Z^-$ represents a monovalent anion.

The following are specific examples of the ammonium ion $G^1G^2G^3G^4N^+$ in the general formula [9].

[Chem. 23]

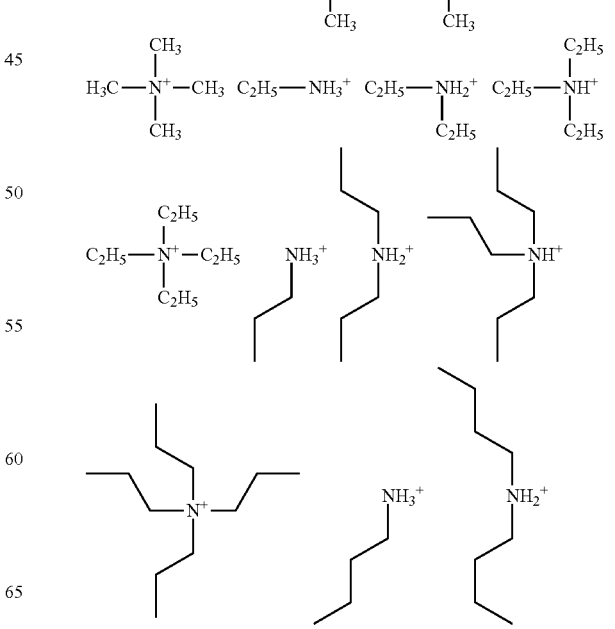

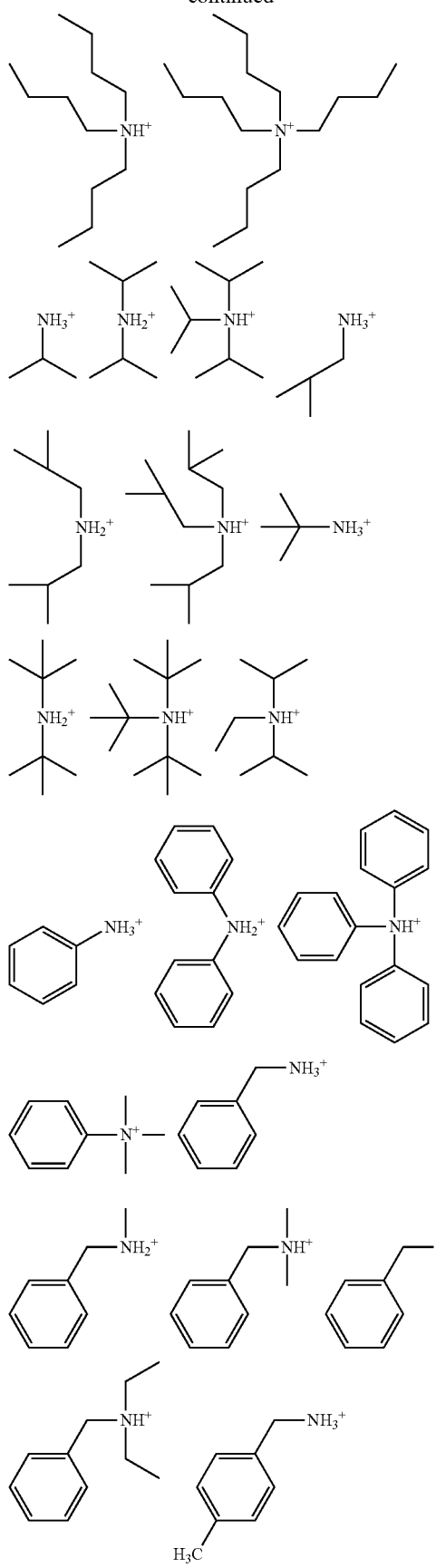
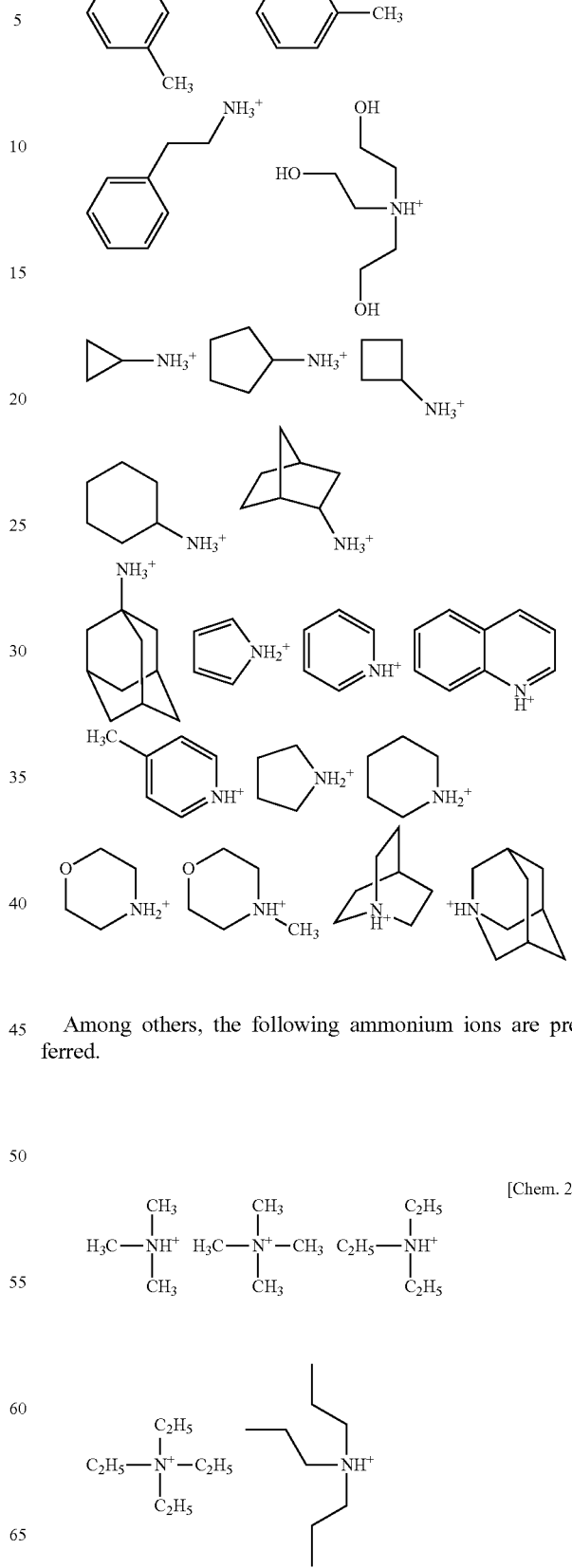
Among others, the following ammonium ions are preferred.
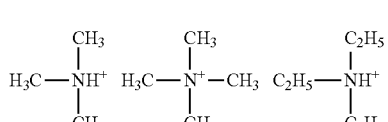

-continued

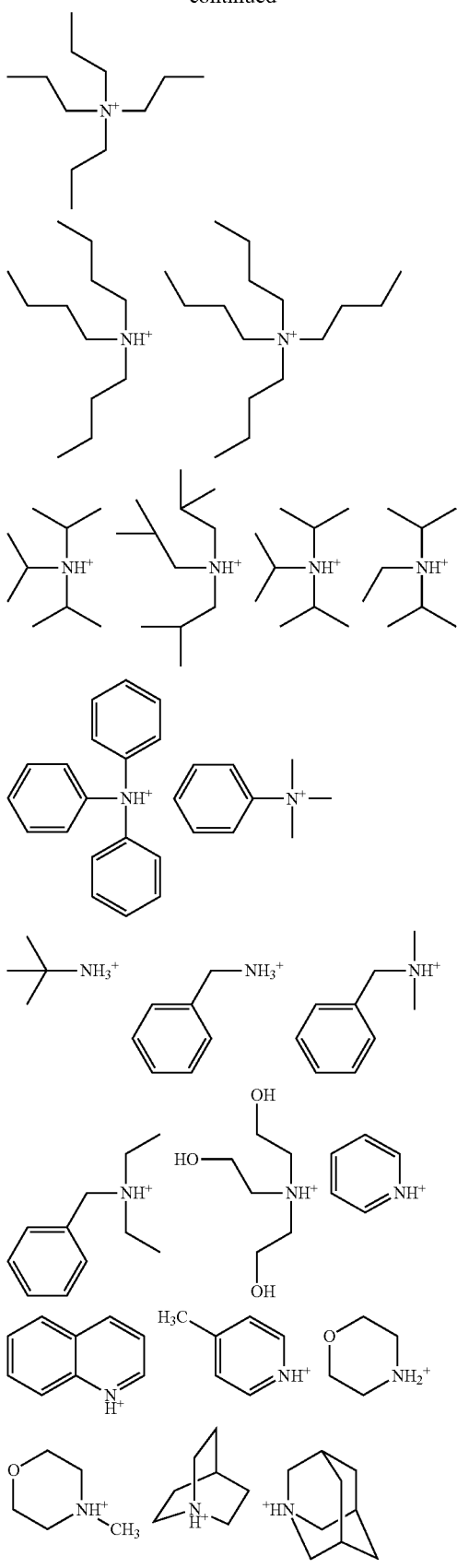

The following ammonium ions are particularly preferred.

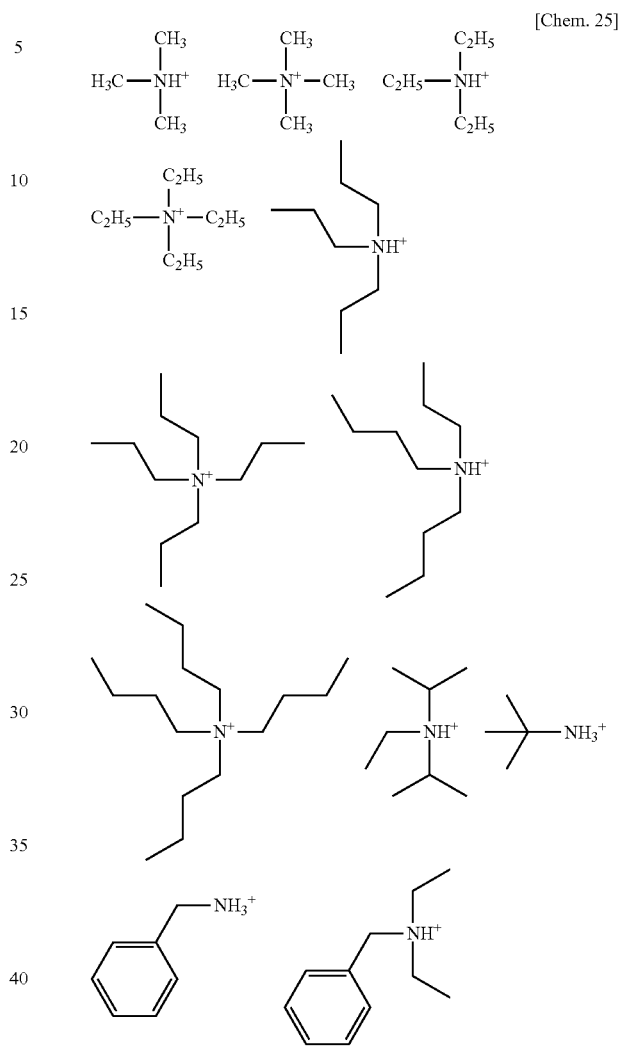

Examples of the monovalent anion $Z^-$ in the general formula [9] are $F^-$, $Cl^-$, $Br^-$, $I^-$, $OH^-$, $ClO_4^-$, $HSO_4^-$, $H_2PO_4^-$, $BF_4^-$, $PF_6^-$, $SbF_6^-$, aliphatic sulfonic acid anions, aromatic sulfonic acid anions, trifluoromethanesulfonic acid anions, fluorosulfonic acid anions, aliphatic carboxylic acid anions, aromatic carboxylic acid anions, fluorocarboxylic acid anions and trifluoroacetic acid anion. Among others, $Cl^-$, $Br^-$, $OH^-$, $HSO_4^-$, $BF_4^-$ and aliphatic sulfonic acid anions are preferred. Particularly preferred are $Cl^-$ and $Br^-$.

The mole ratio of the ammonium salt used relative to the halofluoroalkanoic acid ester [2] is generally in the range of 1.0 to 10.0, preferably 1.1 to 2.0. If the mole ratio of the ammonium salt is less than 1.0, there occurs as a by-product alkoxycarbonylfluoroalkanesulfinic acid metal salt etc. due to the presence of a cation (a metal cation such as sodium ion, potassium ion or lithium ion) derived from the sulfinating agent. In this case, it becomes unfavorably difficult to separate the ammonium salt from the metal salt by the subsequent post-treatment operation. Further, the yield of the target compound becomes unfavorably deteriorated. There is no problem if the mole ratio of the ammonium salt exceeds 10.0. It is however economically disadvantageous and unfavorable to use such a large amount of ammonium salt.

When the sulfination reaction is performed with the use of either the above amine or ammonium salt, the ammonium ion of the general formula [6] can be introduced as A⁺ appropriately. Suitable examples of the alkoxycarbonylfluoroalkanesulfinic acid ammonium salt [3] are those of the following general formula [7].

[Chem. 26]

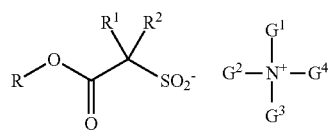

[7]

Preferably, the sulfination reaction is performed in a mixed solvent of an organic solvent and water.

Examples of the organic solvent are those having good compatibility with water, such as lower alcohols, tetrahydrofuran, N,N-dimethylformamide, N,N-dimethylacetamide, acetonitrile and dimethyl sulfoxide. Among others, methanol, N,N-dimethylacetamide, acetonitrile and dimethyl sulfoxide are preferred. Particularly preferred is acetonitrile.

The amount of the organic solvent used is generally 5 parts by weight or more, preferably 10 parts by weight or more, more preferably 20 to 90 parts by weight, per 100 parts by weight of the total amount of the organic solvent and water.

The reaction temperature is generally 0 to 200° C., preferably 20 to 40° C. The reaction time is generally 0.1 to 12 hours, preferably 0.5 to 4 hours. It is desirable to determine the time at which the raw material, i.e., halofluoroalkanoic acid ester [2] has been consumed as the end of the reaction while monitoring the progress of the reaction by any analytical equipment such as thin-layer chromatography (TLC) or nuclear magnetic resonance (NMR).

It is herein noted that, on the condition that the halofluoroalkanoic acid ester [2] of the same structure is used as a substrate of the sulfination reaction, the sulfination reaction requires a higher reaction temperature and a several times to several tens time longer reaction time in the case of using the inorganic acid such as sodium carbonate, potassium carbonate, sodium hydrogencarbonate or potassium hydrogencarbonate than in the case of using the organic base. More specifically, it takes about 8 to 40 hours to perform the sulfination reaction at a reaction temperature of 50 to 80° C. in the case of using the inorganic acid. In this case, the ester moiety of the reaction substrate i.e. halofluoroalkanoic acid ester or the reaction product e.g. alkoxycarbonylfluoroalkanesulfinic acid sodium salt undergoes hydrolysis as the reaction proceeds in the presence of the base. The target sulfination product cannot be thus obtained with high yield. By contrast, the reaction can be promoted significantly by the coexistence of the amine or ammonium salt as the base and thus, in some cases, can be completed within several tens minutes even under moderate reaction conditions. As the hydrolysis of the ester moiety does take place, the target sulfination product can be obtained with high yield. As explained above, it is one effect of the use of the amine or ammonium salt in the present invention to allow the sulfination reaction to proceed under moderate conditions and save the reaction time significantly.

The reaction solution is subjected to post treatment operation as appropriate.

In the present invention, the lipid solubility of the alkoxycarbonylfluoroalkanesulfinic acid ammonium salt [3] are improved by the use of the amine or ammonium salt in the first step. As a result, the target sulfinic acid ammonium salt can be extracted from the reaction solution (uniformly mixed liquid of water and high water-compatible organic solvent, or liquid of two separable water-containing organic layer and organic solvent-containing aqueous layer) by the use of a low water-soluble or water-insoluble organic solvent. Examples of such a solvent are: halogenated solvents such as chloroform and dichloromethane, ether solvents such as diethyl ether, diisopropyl ether and tert-butyl methyl ether; and acetic ester solvents such as ethyl acetate and butyl acetate.

By washing the resulting organic phase with water etc., an inorganic substance including a metal content such as sodium mixed in the organic layer can be removed. It is possible to reduce a load on the purification operation from the next process step onward by reducing, at the present stage, the metal content such as sodium that has been mixed Further, the reaction solution contains a bromine trace equivalent to the amount of the raw material when the sulfination reaction step involves elimination of bromine from the raw material i.e. halofluoroalkanoic acid ester [2]. If the reaction solution with the bromine trace remaining therein is subjected to the next process step, the bromine trace also undergoes oxidation to a chemical species with bromination ability (such as, probably, bromine) so that the raw material i.e. halofluoroalkanoic acid ester [2] becomes by-produced by bromination of the alkoxycarbonylfluoroalkanesulfinic acid ammonium salt [3] with such a chemical species. However, the bromine trace can be processed by extracting the alkoxycarbonylfluoroalkanesulfinic acid ammonium salt [3] with the water-insoluble organic solvent and washing the resulting organic solvent layer with an aqueous solution of metal thiosulfate such as sodium thiosulfate or metal sulfite such as sodium sulfite. This makes it possible to prevent the occurrence of the halofluoroalkanoic acid ester [2] as the by-product of the oxidation reaction of the next process step (see Examples 1-b and 1-c and Comparative Examples 2-a and 2-b).

The mole ratio of the metal thiosulfate such as sodium thiosulfate or metal sulfite such as sodium sulfite used relative to the halofluoroalkanoic acid ester [2] is generally in the range of 0.1 to 10.0, preferably 1.0 to 5.0. Further the concentration of the aqueous metal thiosulfate solution or aqueous metal sulfite solution used is generally 3 wt % to saturation, preferably 5 to 25 wt %.

On the other hand, the alkoxycarbonylfluoroalkanesulfinic acid metal salt obtained by the use of the inorganic salt has a lower lipid solubility and high water solubility than that obtained by the use of the ammonium salt etc. In this case, it is difficult to extract the sulfinic acid metal salt with an organic solvent. Even if the sulfinic acid metal salt can be extracted with an organic solvent, the proportion of the sulfinic acid metal salt partitioned in the aqueous layer is high due to the water solubility of the sulfinic acid metal salt. It is thus difficult to obtain the target sulfinic acid metal salt with high yield. For these reasons, the reaction solution has to be totally concentrated in order that the sulfinic acid metal salt can be obtained with high yield. However, the metal content such as sodium in the reaction solution can hardly be reduced by concentration so that almost all of the metal content used in the reaction would be transferred into the next process step to cause an increase of load on the purification operation from the next process step onward. In addition, the concentration of water is generally more difficult than the concentration of the organic solvent. It is another effect of the use of the organic base in the present invention to increase the lipid solubility of the target sulfination product so as to not only improve the yield of the target sulfination product and the efficiency of the isolation operation but also improve the ease of removal of the inorganic purity including metal content such as sodium etc. as explained above.

In this way, the target sulfinic acid ammonium salt can be obtained by e.g. extracting the reaction solution with the organic solvent, washing the organic layer with water and aqueous metal thiosulfate solution (or aqueous metal sulfite solution) and distillating the organic solvent from the organic layer.

[Second Step: Oxidation Reaction]

In the second step, the alkoxycarbonylfluoroalkanesulfinic acid ammonium salt of the general formula [3] is reacted with the oxidizing agent to form the alkoxycarbonylfluoroalkanesulfonic acid ammonium salt of the general formula [1].

[Chem. 27]

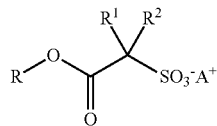

[1]

Examples of the oxidizing agent used in this oxidation reaction step are hydrogen peroxide, m-chloroperoxybenzoic acid, t-butylhydroperoxide, potassium peroxysulfate, potassium permanganate, sodium perborate, sodium metaiodate, chromic acid, sodium dichromate, halogen, iodobenzene chloride, iodobenzene diacetate, osmium (VIII) oxide, ruthenium (VIII) oxide, sodium hypochlorite, sodium chlorite, oxygen gas and ozone gas. Preferred are hydrogen peroxide, m-chloroperoxybenzoic acid and t-butylhydroperoxide.

The mole ratio of the oxidizing agent used relative to the alkoxycarbonylfluoroalkanesulfinic acid ammonium salt [3] is generally in the range of 0.9 to 10.0, preferably 1.0 to 2.0. In the case where the sulfinic acid ammonium salt available as the raw material is in the form of a crude product so that the accurate molar amount of the sulfinic acid ammonium salt is unknown, the oxidizing agent may be added with reference to the molar amount of the halofluoroalkanoic acid ester [2] before the sulfination reaction.

Further, a transition metal catalyst may be used in combination with the oxidizing agent. Examples of the transition metal catalyst are disodium tungstate, iron (III) chloride, ruthenium (III) chloride and selenium (IV) oxide. Among others, disodium tungstate is preferred.

The mole ratio of the transition metal catalyst used relative to the alkoxycarbonylfluoroalkanesulfinic acid ammonium salt [3] is generally in the range of 0.0001 to 1.0, preferably 0.001 to 0.5, more preferably 0.001 to 0.1.

For pH adjustment, a buffering agent may be used in addition to the oxidizing agent and the transition metal catalyst.

Example of the buffering agent are disodium hydrogenphosphate, sodium dihydrogenphosphate, dipotassium hydrogenphosphate and potassium dihydrogenphosphate.

The mole ratio of the buffering agent used relative to the alkoxycarbonylfluoroalkanesulfinic acid ammonium salt [3] is generally in the range of 0.01 to 2.0, preferably 0.03 to 1.0, more preferably 0.05 to 0.5.

In general, the oxidization reaction is performed in a reaction solvent.

Examples of the reaction solvent are water and organic solvents such as lower alcohols, tetrahydrofuran, N,N-dimethylformamide, N,N-dimethylacetamide, acetonitrile, dimethyl sulfoxide, acetic acid, trifluoroacetic acid, chloroform and dichloromethane. Among others, water, methanol, N,N-dimethylacetamide, acetonitrile, dimethyl sulfoxide, chloroform and dichloromethane. Particularly preferred are water, methanol, chloroform and dichloromethane.

Water and the organic solvent can be used in combination as needed. In this case, the amount of the organic solvent used is generally 5 parts by weight or more, preferably 10 parts by weight or more, more preferably 20 to 90 parts by weight, per 100 parts by weight of the mixture of the water and organic solvent. The amount of the reaction solvent used is generally 1 to 100 parts by weight, preferably 2 to 100 parts by weight, more preferably 5 to 50 parts by weight, per 1 part by weight of the alkoxycarbonylfluoroalkanesulfinic acid ammonium salt [3].

The reaction temperature is generally 0 to 100° C., preferably 5 to 60° C., more preferably 5 to 40° C. The reaction time is generally 0.1 to 72 hours, preferably 0.5 to 24 hours, more preferably 0.5 to 12 hours. It is desirable to determine the time at which the raw material, i.e., alkoxycarbonylfluoroalkanesulfinic acid ammonium salt [3] has been consumed as the end of the reaction while monitoring the progress of the reaction by any analytical equipment such as thin-layer chromatography (TLC) or nuclear magnetic resonance (NMR).

The resulting reaction solution is subjected to post treatment operation as appropriate.

The lipid solubility of the alkoxycarbonylfluoroalkanesulfonic ammonium salt [1] are improved due to the use of the amine or ammonium salt in the first step as mentioned above. The target sulfonic acid ammonium salt can be thus extracted from the reaction solution (whose main component is generally water or methanol) by the use of a low water-soluble or water-insoluble organic solvent. Examples of such a solvent are: halogenated solvents such as chloroform and dichloromethane, ether solvents such as diethyl ether, diisopropyl ether and tert-butyl methyl ether; and acetic ester solvents such as ethyl acetate and butyl acetate.

By washing the resulting organic phase with water etc., an inorganic substance including a metal content such as sodium mixed in the organic layer can be removed. It is possible to reduce a load on the purification operation from the next process step onward and to improve the purity of the alkoxycarbonylfluoroalkanesulfonic acid ammonium salt [1] by reducing, at the present stage, the metal content such as sodium that has been mixed into the reaction solution up until the this process step (see Examples 1-b, 1-c, 4-a, 4-b, 5-a and 5-b and Comparative Examples 1-a, 1-b, 2-a and 2-b).

In this case, the amount of the water used is generally 1 to 100 parts by weight, preferably 2 to 100 parts by weight, more preferably 5 to 50 parts by weight, per 1 part by weight of the alkoxycarbonylfluoroalkanesulfinic acid ammonium salt [3].

It is a particularly preferred example of the post treatment operation to, after washing the organic layer with water, measure the metal content such as sodium in the organic layer by metal analysis method such as ion chromatography or ICP mass analysis, compare the measured metal content with a preset standard metal content value and, when the measured metal content exceed the standard value, again wash the organic layer again with water.

[Third Step: Onium Salt Exchange Reaction]

In the third step, the alkoxycarbonylfluoroalkanesulfonic acid onium salt of the general formula [4] is obtained by onium salt exchange reaction of the alkoxycarbonylfluoroalkanesulfonic acid ammonium salt of the general formula [1] with the monovalent onium salt of the general formula [5].

[Chem. 28]

$Q^+X^{-}$ [5]

In the general formula [5], $Q^+$ represents an onium cation selected from a sulfonium cation of the following general formula (a), a sulfonium cation of the following general formula (b) and an iodonium cation of the following general formula (c); and $X^{t-}$ represents a monovalent anion.

[Chem. 29]

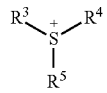

(a)

In the general formula (a), $R^3$, $R^4$ and $R^5$ each independently represent a substituted or unsubstituted $C_1$-$C_{10}$ straight or branched alkyl, alkenyl or oxoalkyl group, or a substituted or unsubstituted $C_6$-$C_{18}$ aryl, aralkyl or aryloxoalkyl group; and two or more of $R^3$, $R^4$ and $R^5$ may be bonded to each other to form a ring with a sulfur atom in the formula.

[Chem. 30]

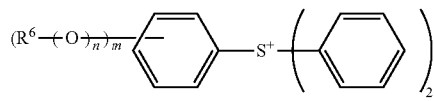

(b)

In the general formula (b), $R^6$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; and n represents 0 (zero) or 1.

[Chem. 31]

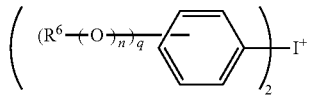

(c)

In the general formula (c), $R^6$ represents a substituted or unsubstituted $C_1$-$C_{20}$ straight, branched or cyclic alkyl or alkenyl group, or a substituted or unsubstituted $C_6$-$C_{14}$ aryl group; q represents an integer of 0 (zero) to 5; and n represents 0 (zero) or 1.

[Sulfonium Cation of General Formula (a)]

Herein, $R^3$, $R^4$ and $R^5$ of the general formula (a) are exemplified as follows. Examples of the alkyl group as $R^3$, $R^4$ and $R^5$ are methyl, ethyl, n-propyl, isopropyl, cyclopropyl, n-butyl, sec-butyl, isobutyl, tert-butyl, n-pentyl, cyclopentyl, n-hexyl, n-heptyl, 2-ethylhexyl, cyclohexyl, cycloheptyl, 4-methylcyclohexyl, cyclohexylmethyl, n-octyl, n-decyl, 1-adamantyl, 2-adamantyl, bicyclo[2.2.1]heptene-2-yl, 1-adamantanemethyl and 2-adamantanemethyl. Examples of the alkenyl group as $R^3$, $R^4$ and $R^5$ are vinyl, allyl, propenyl, butenyl, hexenyl and cyclohexenyl. Examples of the oxoalkyl group as $R^3$, $R^4$ and $R^5$ are 2-oxocyclopentyl, 2-oxocyclohexyl, 2-oxopropyl, 2-oxoethyl, 2-cyclopentyl-2-oxoethyl, 2-cyclohexyl-2-oxoethyl and 2-(4-methylcyclohexyl)-2-oxoethyl. Examples of the aryl group as $R^3$, $R^4$ and $R^5$ are: phenyl; naphthyl; thienyl; alkoxylphenyl groups such as p-methoxyphenyl, m-methoxyphenyl, o-methoxyphenyl, p-ethoxypenyl, p-tert-butoxyphenyl and m-tert-butoxyphenyl; alkylphenyl groups such as 2-methylphenyl, 3-methylphenyl, 4-methylphenyl and ethylphenyl; alkylnaphthyl groups such as methylnaphthyl and ethylnaphthyl; dialkylnaphthyl groups such as diethylnaphthyl; and dialkoxynaphthyl groups such as dimethoxynaphthyl and diethoxynaphthyl. Examples of the aralkyl group as $R^3$, $R^4$ and $R^5$ are benzyl, 1-phenylethyl and 2-phenylethyl. Examples of the aryloxoalkyl group as $R^3$, $R^4$ and $R^5$ are 2-aryl-2-oxoethyl groups such as 2-phenyl-2-oxoethyl, 2-(1-naphthyl)-2-oxoethyl and 2-(2-naphthyl)-2-oxoethyl. In the case where two or more of $R^3$, $R^4$ and $R^5$ are bonded to each other to form a ring structure with the sulfur atom, there can be used 1,4-butylene and 3-oxa-1,5-penthylene. There can also be used aryl groups with polymerizable substituents such as acryloyloxy and methacryloyloxy. Examples of the aryl groups with the polymerizable substituents are 4-(acryloyloxy)phenyl, 4-(methacryloyloxy)phenyl, 4-vinyloxyphenyl and 4-vinylphenyl.

Specific examples of the sulfonium cation of the general formula (a) are triphenylsulfonium, (4-tert-butylphenyl) diphenylsulfonium, bis(4-tert-butylphenyl)phenylsulfonium, tris(4-tert-butylphenyl)sulfonium, (3-tert-butylphenyl) diphenylsulfonium, bis(3-tert-butylphenyl) phenylsulfonium, tris(3-tert-buthylphenyl)sulfonium, (3,4-di-tert-butylphenyl)diphenylsulfonium, bis(3,4-di-tert-butylphenyl)phenylsulfonium, tris(3,4-di-tert-butylphenyl) sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl) diphenylsulfonium, bis(3-tert-butoxyphenyl) phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl) sulfonium, (4-tert-butoxycarbonylmethyloxyphenyl) diphenylsulfonium, tris(4-tert-butoxycarbonylmethyloxyphenyl)sulfonium, (4-tert-butoxyphenyl)bis(4-dimethylaminophenyl)sulfonium, tris (4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl 2-thienylsulfonium, 4-n-butoxynaphthyl-1-thiacyclopentanium, 2-n-butoxynaphthyl-1-thiacyclopentanium, 4-methoxynaphthyl-1-thiacyclopentanium and 2-methoxynaphthyl-1-thiacyclopentanium. Among others, preferred are triphenylsulfonium, (4-tert-buthylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium.

Further, 4-(methacryloyloxy)phenyldiphenylsulfonium, 4-(acryloyloxy)phenyldiphenylsulfonium, 4-(methacryloyloxy)phenyldimethylsulfonium and 4-(acryloyloxy)phenyldimethylsulfonium are also specific examples of the sulfonium cation of the general formula (a). These polymerizable sulfonium cations are disclosed in Japanese Laid-Open Patent Publication No. 4-230645, Japanese Laid-Open Patent Publication No. 2005-84365 and the like.

[Sulfonium Cation of General Formula (b)]

There is no particular limitation on the substitution position of $R^6$—$(O)_n$—. It is preferable that $R^6$—$(O)_n$— is in 4- or 3-position, more preferably 4-position, of the phenyl group. Herein, p represents 0 or 1. Examples of $R^6$ are methyl, ethyl, n-propyl, sec-propyl, cyclopropyl, n-butyl, sec-butyl, iso-butyl, tert-butyl, n-pentyl, cyclopentyl, n-hexyl, cyclohexyl, n-octyl, n-decyl, n-dodecyl, 1-adamantyl, 2-adamantyl, bicyclo[2.2.1]heptene-2-yl, phenyl, 4-methoxyphenyl, 4-tert-butylphenyl, 4-biphenyl, 1-naphthyl, 2-naphthyl, 10-anthranyl and 2-furanyl. In the case of n=1, acryloyl, methacryloyl, vinyl and allyl are usable.

Specific examples of the sulfonium cation of the general formula (b) are (4-methylphenyl)diphenylsulfonium, (4-ethylphenyl)diphenylsulfonium, (4-cyclohexylphenyl)diphenylsulfonium, (4-n-hexylphenyl)diphenylsulfonium, (4-n-octylphenyl)diphenylsulfonium, (4-methoxyphenyl)diphenylsulfonium, (4-ethoxyphenyl)diphenylsulfonium, (4-tert-butoxyphenyl)diphenylsulfonium, (4-cyclohexyloxyphenyl)diphenylsulfonium, (4-trifluoromethylphenyl)diphenylsulfonium, (4-trifluoromethyloxyphenyl)diphenylsulfonium and (4-tert-butoxycarbonylmethyloxyphenyl)diphenylsulfonium.

[Iodonium Cation of General Formula (c)]

There is no particular limitation on the substitution position of $R^6-(O)_n-$. It is preferable that $R^6-(O)_n-$ is in 4- or 3-position, more preferably 4-position, of the phenyl group. Herein, n represents 0 or 1. Examples of $R^6$ in the general formula (c) are the same as those in the general formula (b).

Specific examples of the iodonium cation of the general formula (c) are diphenyl iodonium, bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium and (4-methacryloyloxy)phenylphenyliodonium. Among others, bis(4-tert-butylphenyl)iodonium is preferred.

Examples of the monovalent anion $X^-$ in the general formula [5] are $F^-$, $Cl^-$, $Br^-$, $I^-$, $ClO_4^-$, $HSO_4^-$, $H_2PO_4^-$, $BF_4^-$, $PF_6^-$, $SbF_6^-$, aliphatic sulfonic acid anions, aromatic sulfonic acid anions, trifluoromethanesulfonic acid anions, fluorosulfonic acid anions, aliphatic carboxylic acid anions, aromatic carboxylic acid anions, fluorocarboxylic acid anions and trifluoroacetic acid anion. Among others, $Cl^-$, $Br^-$, $HSO_4^-$, $BF_4^-$ and aliphatic sulfonic acid anions are preferred. Particularly preferred are $Cl^-$, $Br^-$ and $HSO_4^-$.

The mole ratio of the monovalent onium salt [4] used relative to the alkoxycarbonylfluoroalkanesulfonic acid ammonium salt [1] is generally in the range of 0.5 to 10.0, preferably 0.8 to 2.0, more preferably 0.9 to 1.2.

In general, the onium salt exchange reaction is performed in a reaction solvent.

Examples of the reaction solvent are water and organic solvents such as lower alcohols, tetrahydrofuran, N,N-dimethylformamide, N,N-dimethylacetamide, acetonitrile and dimethyl sulfoxide. Among others, water, methanol, N,N-dimethylacetamide, acetonitrile, dimethyl sulfoxide, chloroform and dichloromethane. Particularly preferred is water.

Water and the organic solvent may be used in combination as needed. In this case, the amount of the organic solvent used is generally 5 parts by weight or more, preferably 10 parts by weight or more, more preferably 20 to 90 parts by weight, per 100 parts by weight of the mixture of the water and organic solvent.

The reaction temperature is generally 0 to 80° C., preferably 5 to 30° C. The reaction time is generally 10 minutes to 16 hours, preferably 30 minutes to 6 hours. It is desirable to determine the time at which the raw material, i.e., alkoxycarbonylfluoroalkanesulfonic acid ammonium salt [1] has been consumed as the end of the reaction while monitoring the progress of the reaction by any analytical equipment such as thin-layer chromatography (TLC) or nuclear magnetic resonance (NMR).

The thus-obtained alkoxycarbonylfluoroalkanesulfonic acid onium salt of the general formula [4] may be purified as needed by washing with or extracting with an organic solvent. It is preferable to use the organic solvent that does not mix with water. Examples of such a solvent are: esters such as ethyl acetate and n-butyl acetate; ethers such as diethyl ether; and halogenated alkyl compounds such as methylene chloride and chloroform.

In the case of using the inorganic base in the sulfination reaction step, the metal content such as sodium remains in the alkoxycarbonylfluoroalkanesulfonic acid onium salt obtained by onium salt exchange reaction of the alkoxycarbonylfluoroalkanesulfonic acid metal salt. It is difficult to remove the metal content from the sulfonic acid onium salt for the reasons that the onium salt exchange reaction uses a salt of metal, typically sodium as a substrate and that the alkoxycarbonylfluoroalkanesulfonic acid metal salt contains a large amount of inorganic impurity including metal salt.

In the present invention, on the other hand, no metal content remains in the alkoxycarbonylfluoroalkanesulfonic acid ammonium salt itself. Further, the alkoxycarbonylfluoroalkanesulfonic acid ammonium salt as well as the alkoxycarbonylfluoroalkanesulfinic acid ammonium salt obtained in the first step can be extracted with the organic solvent and washed with water so as to significantly reduce the inorganic impurity including metal such as sodium in the ammonium salt as mentioned above. Thus, there is almost no metal content such as sodium remaining in the alkoxycarbonylfluoroalkanesulfonic acid onium salt obtained by onium salt exchange reaction of the alkoxycarbonylfluoroalkanesulfonic acid ammonium salt (see Examples 1-d, 4-c and 5-c and Comparative Example 1-c).

EXAMPLES

The present invention will be described in more detail below by way of the following examples. It should be noted that these examples are illustrative and are not intended to limit the present invention thereto.

Example 1-a

Production of bromodifluoroacetic acid adamantane-1-ylmethyl ester

Pretreatment Step: Esterification Reaction

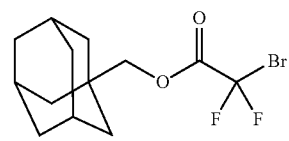

[Chem. 32]

Into a 50-L reaction vessel, 476 g (3.18 mol, 1.11 eq) of 1-adamantanemethanol and 5.5 kg of diethyl ether were added. The resulting solution was suspended by stirring, followed by adding thereto 615 g (2.86 mol, 1.0 eq) of bromodifluoroacetyl chloride. The suspended solution was cooled down to 0° C. Then, 578 g (5.72 mol, 2.0 eq) of triethylamine was slowly dropped to the cooled suspended solution. This reaction solution was left, while stirring, until it reached room temperature. The reaction solution was further stirred for 1 hour at room temperature. Subsequently, the reaction solution was washed with 5 kg of water. The thus-obtained organic layer was washed with 5 kg of saturated sodium hydrogencarbonate solution, with 5 kg of saturated sodium chloride solution, and then, with 5 kg of water. The washed organic layer was dried with magnesium sulfate and subjected to solvent distillation. With this, 878 g of target bromodifluoroacetic acid adamantane-1-ylmethyl ester was obtained (yield: 95%, purity: 100%).

[Properties of bromodifluoroacetic acid adamantane-1-ylmethyl ester]

$^1$H NMR (measurement solvent: deuterium chloroform, reference material: tetramethylsilane); δ=3.92 (s, 2H; CH$_2$), 2.00 (m, 3H; 1-Ad), 1.62 (m, 12H, 1-Ad).

$^{19}$F NMR (measurement solvent: deuterium chloroform, reference material: trichlorofluoromethane); δ=−60.76 (s, 2F; CF$_2$).

No fluorine ion (F$^−$) was detected from any liquid waste of this step.

Example 1-b

Production of (adamantane-1-ylmethyl)oxycarbonyldifluoromethanesulfinic acid triethylammonium salt First Step: Sulfination Reaction, Extraction Solvent: Chloroform

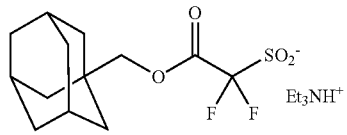

[Chem. 33]

Within a 3-L three-neck flask, 200 g (618 mmol, 1.0 eq) of the bromodifluoroacetic acid adamantane-1-ylmethyl ester obtained in Example 1-a was dissolved in 600 g of acetonitrile. Into the resulting solution, 500 g of water and 129.2 g (740 mmol, 1.2 eq) of sodium dithionite were added and stirred. Further, 65.6 g (648 mmol, 1.05 eq) of triethylamine was added into the solution at a temperature range of 20 to 35° C. This reaction solution was then stirred for 0.5 hour. After the reaction, the reaction solution was separated into an organic layer and an aqueous layer. The organic layer was converted to a chloroform solution by distillating acetonitrile from the organic layer and adding 600 g of chloroform to the distillation residue. The thus-obtained organic layer was washed once with 10% aqueous sodium thiosulfate solution and washed once with water. By distillation of chloroform from the washed organic layer, 246 g of target (adamantane-1-ylmethyl)oxycarbonyldifluoromethanesulfinic acid triethylammonium salt was obtained. The purity of the target compound was 86%; and the yield of the target compound was 84%.

[Properties of (adamantane-1-ylmethyl)oxycarbonyldifluoromethanesulfinic acid triethylammonium salt]

$^1$H NMR (measurement solvent: deuterium dimethylformamide, reference material: tetramethylsilane); δ=3.75 (s, 2H; CH$_2$), 3.07 (q, J=7.5 Hz, 6H; Et$_3$N), 1.91 (m, 3H; 1-Ad), 1.61 (m, 6H; 1-Ad), 1.49 (m, 6H; 1-Ad), 1.17 (t, J=7.5 Hz, 9H; Et$_3$N).

$^{19}$F NMR (measurement solvent: deuterium dimethylformamide, reference material: trichlorofluoromethane); δ=−120.92 (s, 2F; CF$_2$).

A slight amount (26 ppm) of fluorine ion (F$^−$) was detected from the aqueous layer of the reaction solution of this step. Further, 5150 ppb of sodium ion (Na$^+$) was detected from the (adamantane-1-ylmethyl)oxycarbonyldifluoromethanesulfinic acid triethylammonium salt obtained in this step.

Example 1-c

Production of (adamantane-1-ylmethyl)oxycarbonyldifluoromethanesulfonic acid triethylammonium salt Second Step: Oxidation Reaction, Extraction Solvent: Chloroform

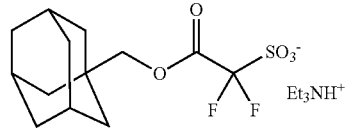

[Chem. 34]

Within a 1-L three-neck flask, 120 g (purity: 86%, 252 mmol, 1.0 eq) of the (adamantane-1-ylmethyl)oxycarbonyldifluoromethanesulfinic acid triethylammonium salt obtained in Example 1-b was dissolved in 400 g of water. To the resulting solution, 0.125 g (0.378 mmol, 0.0015 eq) of disodium tungstate dihydrate and 34.3 g (302 mmol, 1.2 eq) of 30% hydrogen peroxide were added. This reaction solution was stirred for 2 hours at room temperature. After that, it was confirmed by $^{19}$F NMR of the reaction solution that: the (adamantane-1-ylmethyl)oxycarbonyldifluoromethanesulfinic acid triethylammonium salt was totally consumed; and there was less than 1% of bromodifluoroacetic acid adamantane-1-ylmethyl ester as a by-product. The reaction solution was extracted twice with 250 g of chloroform. The thus-obtained organic layer was washed once with water. By distillation of chloroform from the washed organic layer, 112 g of target (adamantane-1-ylmethyl)oxycarbonyldifluoromethanesulfonic acid triethylammonium salt was obtained. The purity of the target compound was 93%; and the yield of the target compound was 97%.

[Properties of (adamantane-1-ylmethyl)oxycarbonyldifluoromethanesulfonic acid triethylammonium salt]

$^1$H NMR (measurement solvent: deuterium dimethylformamide, reference material: tetramethylsilane); δ=3.80 (s, 2H; CH$_2$), 3.10 (q, J=7.5 Hz, 6H; Et$_3$N), 1.91 (m, 3H; 1-Ad), 1.62 (m, 6H; 1-Ad), 1.50 (m, 6H; 1-Ad), 1.17 (t, J=7.5 Hz, 9H; Et$_3$N).

$^{19}$F NMR (measurement solvent: deuterium dimethylformamide, reference material: trichlorofluoromethane); δ=−108.56 (s, 2F; CF$_2$).

No fluorine ion (F$^−$) was detected from any liquid waste of this step. Further, 1580 ppb of sodium ion (Na$^+$) was detected from the (adamantane-1-ylmethyl)oxycarbonyldifluoromethanesulfonic acid triethylammonium salt obtained in this step.

Example 1-d

Production of triphenylsulfonium (adamantane-1-ylmethyl)oxycarbonyldifluoromethanesulfonate Third Step: Onium Salt Exchange Reaction

[Chem. 35]

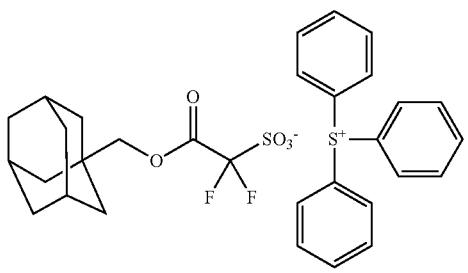

Within a 1-L three-neck flask, 100 g (purity: 93%, 219 mmol, 1.0 eq) of the (adamantane-1-ylmethyl)oxycarbonyldifluoromethanesulfonic acid triethylammonium salt obtained in Example 1-c was dissolved in 300 g of chloroform. To the resulting solution, 250 g of water and 78.9 g (223 mmol, 1.05 eq) of triphenylsulfonium bromide were added. This reaction solution was stirred for 1 hour. After the reaction, the reaction solution was separated into an organic layer and an aqueous layer. The organic layer was washed with water, followed by distillating chloroform from the washed organic layer. The thus-obtained concentrated solution was dissolved in a mixed solvent of chloroform, ethyl acetate and diisopropyl ether and then recrystallized. With this, 119 g of target triphenylsulfonium (adamantane-1-ylmethyl)oxycarbonyldifluoromethanesulfonate was obtained (yield: 92%, purity: 99%).

[Properties of triphenylsulfonium (adamantane-1-ylmethyl)oxycarbonyldifluoromethanesulfonate]

$^1$H NMR (measurement solvent: deuterium chloroform, reference material: tetramethylsilane); δ=7.72 (m, 15H; TPS), 3.85 (s, 2H; CH$_2$), 1.92 (m, 3H; 1-Ad), 1.62 (m, 12H; 1-Ad).

$^{19}$F NMR (measurement solvent: deuterium chloroform, reference material: trichlorofluoromethane); δ=−110.0 (s, 2F; CF$_2$).

No fluorine ion (F$^-$) was detected from any liquid waste of this step. Further, 440 ppb of sodium ion (Na$^+$) was detected from the triphenylsulfonium (adamantane-1-ylmethyl)oxycarbonyldifluoromethanesulfonate obtained in this step.

Example 2-a

Production of (adamantane-1-ylmethyl)oxycarbonyldifluoromethanesulfinic acid triethylammonium salt First Step: Sulfination Reaction, Extraction Solvent: Dichloromethane The reaction was performed in the same manner as in Example 1-b. After the reaction, the reaction solution was separated into an organic layer and an aqueous layer. The organic layer was converted to a dichloromethane solution by distillating acetonitrile from the organic layer and adding 300 g of dichloromethane (in place of chloroform) to the distillation residue. The thus-obtained organic layer was washed once with 10% aqueous sodium thiosulfate solution and washed once with water. By distillation of dichloromethane from the washed organic layer, 112 g of target (adamantane-1-ylmethyl)oxycarbonyldifluoromethanesulfinic acid triethylammonium salt was obtained. The purity of the target compound was 89%; and the yield of the target compound was 79%. A slight amount (15 ppm) of fluorine ion (F$^-$) was detected from the aqueous layer of the reaction solution of this step. Further, 4500 ppb of sodium ion (Na$^+$) was detected from the (adamantane-1-ylmethyl)oxycarbonyldifluoromethanesulfinic acid triethylammonium salt obtained in this step.

Example 2-b

Production of (adamantane-1-ylmethyl)oxycarbonyldifluoromethanesulfonic acid triethylammonium salt Second Step: Oxidation Reaction, Extraction Solvent: Dichloromethane Within a 1-L three-neck flask, 110 g (purity: 89%, 239 mmol, 1.0 eq) of the (adamantane-1-ylmethyl)oxycarbonyldifluoromethanesulfinic acid triethylammonium salt obtained in Example 2-a was dissolved in 400 g of water. To the resulting solution, 0.118 g (0.358 mmol, 0.0015 eq) of disodium tungstate dihydrate and 32.6 g (287 mmol, 1.2 eq) of 30% hydrogen peroxide were added. This reaction solution was stirred for 2 hours at room temperature. After that, it was confirmed by $^{19}$F NMR of the reaction solution that: the (adamantane-1-ylmethyl)oxycarbonyldifluoromethanesulfinic acid triethylammonium salt was totally consumed; and there was less than 1% of bromodifluoroacetic acid adamantane-1-ylmethyl ester as a by-product. The reaction solution was extracted twice with 250 g of dichloromethane (in place of chloroform). The thus-obtained organic layer was washed once with water. By distillation of dichloromethane from the washed organic layer, 109 g of target (adamantane-1-ylmethyl)oxycarbonyldifluoromethanesulfonic acid triethylammonium salt was obtained. The purity of the target compound was 95%; and the yield of the target compound was 96%. No fluorine ion (F$^-$) was detected from any liquid waste of this step. Further, 1170 ppb of sodium ion (Na$^+$) was detected from the (adamantane-1-ylmethyl)oxycarbonyldifluoromethanesulfonic acid triethylammonium salt obtained in this step.

Example 3

Production of (adamantane-1-ylmethyl)oxycarbonyldifluoromethanesulfonic acid triethylammonium salt Second Step: Oxidation Reaction, Increased Number of Water Washing Operations The reaction was performed in the same manner as in Example 1-c. The reaction solution was extracted twice with 250 g of chloroform. The thus-obtained organic layer was washed five times with water (in place of a single water washing operation in Example 1-c). By distillation of chloroform from the washed organic layer, 90.6 g of target (adamantane-1-ylmethyl)oxycarbonyldifluoromethanesulfonic acid triethylammonium salt was obtained. The purity of the target compound was 96%; and the yield of the target compound was 81%. No fluorine ion (F$^-$) was detected from any liquid waste of this step. Further, 420 ppb of sodium ion (Na$^+$) was detected from the (adamantane-1-ylmethyl)oxycarbonyldifluoromethanesulfonic acid triethylammonium salt obtained in this step. As explained above, the present example showed some deterioration in yield but achieved significant reduction in sodium content as compared to Example 1-c.

Example 4-a

Production of (adamantane-1-ylmethyl)oxycarbonyldifluoromethanesulfinic acid tert-butylammonium salt First Step: Sulfination Reaction with Coexistence of Amine

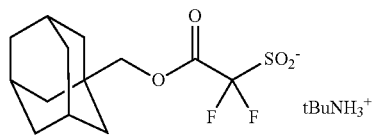

[Chem. 36]

Within a 2-L three-neck flask, 150 g (455 mmol, 1.0 eq) of the bromodifluoroacetic acid adamantane-1-ylmethyl ester obtained in Example 1-a was dissolved in 450 g of acetonitrile. Into the resulting solution, 400 g of water and 95.1 g (546 mmol, 1.2 eq) of sodium dithionite were added and stirred. Further, 36.6 g (501 mmol, 1.1 eq) of tert-butylamine was added into the solution at a temperature range of 20 to 35° C. This reaction solution was then stirred for 1 hour. After the reaction, the reaction solution was separated into an organic layer and an aqueous layer. The organic layer was converted to a chloroform solution by distillating acetonitrile from the organic layer and adding 600 g of chloroform to the distillation residue. The thus-obtained organic layer was washed once with 10% aqueous sodium thiosulfate solution and washed once with water. By distillation of chloroform from the washed organic layer, 165 g of target (adamantane-1-ylmethyl)oxycarbonyldifluoromethanesulfinic acid tert-butylammonium salt was obtained. The purity of the target compound was 84%; and the yield of the target compound was 80%.

[Properties of (adamantane-1-ylmethyl)oxycarbonyldifluoromethanesulfinic acid tert-butylammonium salt]

$^1$H NMR (measurement solvent: deuterium dimethylformamide, reference material: tetramethylsilane); δ=3.75 (s, 2H; CH$_2$), 1.91 (m, 3H; 1-Ad), 1.61 (m, 6H; 1-Ad), 1.49 (m, 6H; 1-Ad), 1.23 (s, 9H; tBuNH$_2$).

$^{19}$F NMR (measurement solvent: deuterium dimethylformamide, reference material: trichlorofluoromethane); δ=−121.01 (s, 2F; CF$_2$).

A slight amount (28 ppm) of fluorine ion (F$^-$) was detected from the aqueous layer of the reaction solution of this step. Further, 5020 ppb of sodium ion (Na$^+$) was detected from the (adamantane-1-ylmethyl)oxycarbonyldifluoromethanesulfinic acid tert-butylammonium salt obtained in this step.

Example 4-b

Production of (adamantane-1-ylmethyl)oxycarbonyldifluoromethanesulfonic acid tert-butylammonium salt Second Step: Oxidation Reaction, Followed by Recrystallization Operation

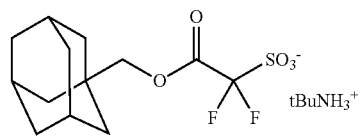

[Chem. 37]

Within a 1-L three-neck flask, 165 g (purity 84%, 364 mmol, 1.0 eq) of the (adamantane-1-ylmethyl)oxycarbonyldifluoromethanesulfinic acid tert-butylammonium salt obtained in Example 4-a was dissolved in 600 g of chloroform. To the resulting solution, 94 g (382 mmol, 1.05 eq) of 70% m-chlorobenzoic acid was slowly added at 0° C. This reaction solution was stirred for 1 hour at room temperature. After that, it was confirmed by $^{19}$F NMR of the reaction solution that: the (adamantane-1-ylmethyl)oxycarbonyldifluoromethanesulfinic acid tert-butylammonium salt was totally consumed; and there was no bromodifluoroacetic acid adamantane-1-ylmethyl ester detected as a by-product. The thus-obtained organic layer was washed with 200 g of 10% aqueous sodium sulfite solution, washed with 500 g of saturated sodium hydrogencarbonate solution and washed twice with 500 g of water. After distillation of chloroform from the washed organic layer, the solid residue was dissolved in a mixed solvent of chloroform, ethyl acetate and diisopropyl ether and then recrystallized. With this, 130 g of target (adamantane-1-ylmethyl)oxycarbonyldifluoromethanesulfonic acid tert-butylammonium salt was obtained. The purity of the target compound was 99%; and the yield of the target compound was 90%.

[Properties of (adamantane-1-ylmethyl)oxycarbonyldifluoromethanesulfonic acid tert-butylammonium salt]

$^1$H NMR (measurement solvent: deuterium dimethylformamide, reference material: tetramethylsilane); δ=3.80 (s, 2H; CH$_2$), 1.91 (m, 3H; 1-Ad), 1.63 (m, 6H; 1-Ad), 1.50 (m, 6H; 1-Ad), 1.20 (s; tBuNH$_2$).

$^{19}$F NMR (measurement solvent: deuterium dimethylformamide, reference material: trichlorofluoromethane); δ=−108.20 (s, 2F; CF$_2$).

No fluorine ion (F$^-$) was detected from any liquid waste of this step. Further, 360 ppb of sodium ion (Na$^+$) was detected from the (adamantane-1-ylmethyl)oxycarbonyldifluoromethanesulfonic acid tert-butylammonium salt obtained in this step. As explained above, the present example showed some deterioration in yield but achieved significant reduction in sodium content as compared to Example 1-b.

Example 4-c

Production of triphenylsulfonium (adamantane-1-ylmethyl)oxycarbonyldifluoromethanesulfonate Third Step: Onium Salt Exchange Reaction Within a 1-L three-neck flask, 130 g (purity 99%, 324 mmol, 1.0 eq) of the (adamantane-1-ylmethyl)oxycarbonyldifluoromethanesulfonic acid tert-butylammonium salt obtained in Example 4-b was dissolved in 500 g of chloroform. To the resulting solution, 400 g of water and 116.8 g (340 mmol, 1.05 eq) of triphenylsulfonium bromide were added. This reaction solution was stirred for 1 hour. After the reaction, the reaction solution was separated into an organic layer and an aqueous layer. The organic layer was washed with water, followed by distillating chloroform from the washed organic layer. The thus-obtained concentrated solution was dissolved in a mixed solvent of chloroform, ethyl acetate and diisopropyl ether and then recrystallized. With this, 176 g of target triphenylsulfonium (adamantine-1-ylmethyl)oxycarbonyldifluoromethanesulfonate was obtained (yield: 93%, purity: 99%). No fluorine ion ($F^-$) was detected from any liquid waste of this step. Further, 220 ppb of sodium ion ($Na^+$) was detected from the triphenylsulfonium (adamantane-1-ylmethyl)oxycarbonyldifluoromethanesulfonate obtained in this step.

Example 5-a

Production of (adamantane-1-ylmethyl)oxycarbonyldifluoromethanesulfinic acid tert-butylammonium salt First Step: Sulfination Reaction with Coexistence of Ammonium Salt Within a 2-L three-neck flask, 150 g (455 mmol, 1.0 eq) of the bromodifluoroacetic acid adamantane-1-ylmethyl ester obtained in Example 1a was dissolved in 450 g of acetonitrile. To the resulting solution, 400 g of water, 59.9 g (546 mmol, 1.2 eq) of tert-butylammonium chloride and 95.1 g (546 mmol, 1.2 eq) of sodium dithionite were added. This reaction solution was stirred for 2 hours. After the reaction, the reaction solution was separated into an organic layer and an aqueous layer. The organic layer was converted to a chloroform solution by distillating acetonitrile from the organic layer and adding 600 g of chloroform to the distillation residue. The thus-obtained organic layer was washed once with 10% aqueous sodium thiosulfate solution and washed once with water. By distillation of chloroform from the washed organic layer, 153 g of target (adamantane-1-ylmethyl)oxycarbonyldifluoromethanesulfinic acid tert-butylammonium salt was obtained. The purity of the target compound was 86%; and the yield of the target compound was 76%. A slight amount (28 ppm) of fluorine ion ($F^-$) was detected from the aqueous layer of the reaction solution of this step. Further, 4930 ppb of sodium ion ($Na^+$) was detected from the (adamantane-1-ylmethyl)oxycarbonyldifluoromethanesulfinic acid tert-butylammonium salt obtained in this step. As explained above, the present example showed that the sulfination reaction could proceed even with the coexistence of the ammonium salt.

Example 5-b

Production of (adamantane-1-ylmethyl)oxycarbonyldifluoromethanesulfonic acid tert-butylammonium salt Second Step: Oxidation Reaction Within a 1-L three-neck flask, 153 g (purity 86%, 345 mmol, 1.0 eq) of the (adamantane-1-ylmethyl)oxycarbonyldifluoromethanesulfinic acid tert-butylammonium salt obtained in Example 5-a was dissolved in 600 g of chloroform. To the resulting solution, 89 g (362 mmol, 1.05 eq) of 70% m-chlorobenzoic acid was slowly added at 0° C. This reaction solution was stirred for 1 hour at room temperature. After that, it was confirmed by $^{19}F$ NMR of the reaction solution that: the (adamantane-1-ylmethyl)oxycarbonyldifluoromethanesulfonic acid tert-butylammonium salt was totally consumed; and there was no bromodifluoroacetic acid adamantane-1-ylmethyl ester detected as a by-product. The thus-obtained organic layer was washed with 200 g of 10% aqueous sodium sulfite solution, washed with 500 g of saturated sodium hydrogencarbonate solution and washed twice with 500 g of water. After distillation of chloroform from the washed organic layer, the solid residue was dissolved in a mixed solvent of chloroform, ethyl acetate and diisopropyl ether and then recrystallized. With this, 122 g of target (adamantane-1-ylmethyl)oxycarbonyldifluoromethanesulfonic acid tert-butylammonium salt was obtained. The purity of the target compound was 99%; and the yield of the target compound was 89%. No fluorine ion ($F^-$) was detected from any liquid waste of this step. Further, 380 ppb of sodium ion ($Na^+$) was detected from the (adamantane-1-ylmethyl)oxycarbonyldifluoromethanesulfonic acid tert-butylammonium salt obtained in this step.

Example 5-c

Production of triphenylsulfonium (adamantane-1-ylmethyl)oxycarbonyldifluoromethanesulfonate Third Step: Onium Salt Exchange Reaction Within a 1-L three-neck flask, 122 g (purity: 99%, 307 mmol, 1.0 eq) of the (adamantane-1-ylmethyl)oxycarbonyldifluoromethanesulfonic acid tert-butylammonium salt obtained in Example 5-b was dissolved in 500 g of chloroform. To the resulting solution, 400 g of water and 110.5 g (322 mmol, 1.05 eq) of triphenylsulfonium bromide were added. This reaction solution was stirred for 1 hour. After the reaction, the reaction solution was separated into an organic layer and an aqueous layer. The organic layer was washed with water, followed by distillating chloroform from the washed organic layer. The thus-obtained concentrated solution was dissolved in a mixed solvent of chloroform, ethyl acetate and diisopropyl ether and then recrystallized. With this, 166 g of target triphenylsulfonium (adamantane-1-ylmethyl)oxycarbonyldifluoromethanesulfonate was obtained (yield: 92%, purity: 99%). No fluorine ion ($F^-$) was detected from any liquid waste of this step. Further, 200 ppb of sodium ion ($Na^+$) was detected from the triphenylsulfonium (adamantane-1-ylmethyl)oxycarbonyldifluoromethanesulfonate obtained in this step.

Comparative Example 1-a

Production of (adamantane-1-ylmethyl)oxycarbonyldifluoromethanesulfinic acid sodium salt First Step: Sulfination Reaction

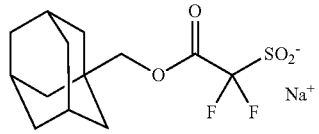

[Chem. 38]

Within a 200-ml three-neck flask, 9.55 g (29.6 mmol, 1.0 eq) of bromodifluoroacetic acid adamantane-1-ylmethyl ester was dissolved in 40 g of acetonitrile. To the resulting solution, 4.96 g (59.0 mmol, 2.0 eq) of sodium hydrogencarbonate and 7.72 g (44.3 mmol, 1.5 eq) of sodium dithionite were added. Further, 40 g of water was added with stirring to the solution. The reaction system was placed in a nitrogen atmosphere. Then, the reaction solution was heated to 50° C. and stirred for 8 hours. After the reaction, the reaction solution was separated into two layers. The organic layer was recovered. The remaining aqueous layer was extracted with 50 g of acetonitrile. The organic layers were combined and subjected to solvent distillation. To the distillation residue, 50 g of diisopropyl ether was added. The thus-obtained suspended solution was stirred for 30 minutes at room temperature and subjected to filtration. The filtrate was then subjected to solvent distillation. With this, 12.4 g of a solid matter containing target (adamantane-1-ylmethyl)oxycarbonyldifluoromethanesulfinic acid sodium salt was obtained. The purity of the target compound was 51%; and the yield of the target compound was 65%. The amount of sodium ion ($Na^+$) in the (adamantane-1-ylmethyl)oxycarbonyldifluoromethanesulfinic acid sodium salt obtained in this step was 1% or more.

Comparative Example 1-b

Production of (adamantane-1-ylmethyl)oxycarbonyldifluoromethanesulfonic acid sodium salt Second Step: Oxidation Reaction

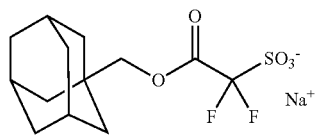

[Chem. 39]

Within a 200-mL three-neck flask, 12.4 g of the solid matter obtained in Comparative Example 1-a, in which the (adamantane-1-ylmethyl)oxycarbonyldifluoromethanesulfinic acid sodium salt was present in an amount of 6.36 g (19.3 mmol, 1.0 eq), was dissolved in 120 ml of water. To the resulting solution, 5.03 g (44.4 mmol, 2.3 eq) of 30% hydrogen peroxide and 15 mg (0.045 mmol, 0.0024 eq) of sodium tungstate (VI) dihydrate were added. This reaction solution was stirred for 1.5 hour at room temperature. After distillation of water from the reaction solution, the distillation residue was dried. With this, 9.84 g of a solid matter containing target (adamantane-1-ylmethyl)oxycarbonyldifluoromethanesulfonic acid sodium salt was obtained. The purity of the target compound was 66%; and the yield of the target compound was 97%. The amount of sodium ion ($Na^+$) in the (adamantane-1-ylmethyl)oxycarbonyldifluoromethanesulfonic acid sodium salt obtained in this step was 1% or more.

Comparative Example 1-c

Production of triphenylsulfonium (adamantane-1-ylmethyl)oxycarbonyldifluoromethane sulfonate Third Step: Onium Salt Exchange Reaction Within a 200-mL three-neck flask, 83 g of water was added to 8.86 g of the solid matter obtained in Comparative Example 1-b, in which the (adamantane-1-ylmethyl)oxycarbonyldifluoromethanesulfonic acid sodium salt was present in an amount of 5.85 g (16.9 mmol, 1.0 eq). The resulting mixture was suspended by stirring and then heated to 80° C. The suspension was turned into a uniform solution when it reached 80° C. Into this solution, 100 g of chloroform and 6.1 g (17.7 mmol, 1.05 eq) of triphenylsulfonium bromide were added. The reaction solution was then stirred for 1 hour. After the reaction, the reaction solution was separated into an organic layer and an aqueous layer. The organic layer was washed with water, followed by distillating chloroform from the washed organic layer. The thus-obtained concentrated solution was dissolved into a mixed solvent of chloroform, ethyl acetate and diisopropyl ether and then recrystallized. With this, 9.0 g of target triphenylsulfonium (adamantane-1-ylmethyl)oxycarbonyldifluoromethane sulfonate was obtained (yield: 90%, purity: 99%). Further, 3180 ppb of sodium ion ($Na^+$) was detected from the triphenylsulfonium (adamantane-1-ylmethyl)oxycarbonyldifluoromethane sulfonate obtained in this step.

Comparative Example 2-a

Production of (adamantane-1-ylmethyl)oxycarbonyldifluoromethanesulfonic acid ammonium salt (First step: sulfination reaction)

Comparative Example 2-b

Production of (adamantane-1-ylmethyl)oxycarbonyldifluoromethanesulfonic acid triethylammonium salt Second Step: Oxidation Reaction Within a 300-mL three-neck flask, 69 g (purity: 62%, 105 mmol, 1.0 eq) of the above-obtained (adamantane-1-ylmethyl)oxycarbonyldifluoromethanesulfinic acid triethylammonium salt was dissolved in 200 g of water. To the resulting solution, 0.052 g (0.157 mmol, 0.0015 eq) of disodium tungstate dihydrate and 16.7 g (147 mmol, 1.4 eq) of 30% hydrogen peroxide were added. This reaction solution was stirred for 4 hours at room temperature. After that, it was confirmed by $^{19}$F NMR of the reaction solution that: the (adamantane-1-ylmethyl)oxycarbonyldifluoromethanesulfinic acid triethylammonium salt was totally consumed; and there was 21% of bromodifluoroacetic acid adamantane-1-ylmethyl ester as a by-product. The reaction solution was extracted twice with 100 g of dichloromethane. The thus-obtained organic layer was washed with water and washed with aqueous sodium chloride solution. By distillation of dichloromethane from the washed organic layer, 46 g of target (adamantane-1-ylmethyl)oxycarbonyldifluoromethanesulfonic acid triethylammonium salt was obtained. The purity of the target compound was 71%; and the yield of the target compound was 74%. The amount of sodium ion (Na$^+$) in the (adamantane-1-ylmethyl)oxycarbonyldifluoromethanesulfonic acid triethylammonium salt obtained in this step was 1% or more.

The above results are summarized with respect to the yield in TABLE 1 and with respect to the sodium ion amount in TABLE 2.

TABLE 1

| Yield (unit: %) | Example 1 | Example 2 | Example 3 | Example 4 |
|---|---|---|---|---|
| First step: sulfination | 84 (Example 1-b) | 79 (Example 2-a) | | 80 (Example 4-a) |
| Second step: oxidation | 97 (Example 1-c) | 96 (Example 2-b) | 81 (Example 3) | 90 (Example 4-b) |
| Third step: onium ion exchange | 92 (Example 1-d) | | | 93 (Example 4-c) |

| Yield (unit: %) | Example 5 | Comparative Example 1 | Comparative Example 2 |
|---|---|---|---|
| First step: sulfination | 76 (Example 5-a) | 51 (Comparative Example 1-a) | 85 (Comparative Example 2-a) |
| Second step: oxidation | 89 (Example 5-b) | 97 (Comparative Example 1-b) | 74 (Comparative Example 2-b) |
| Third step: onium ion exchange | 92 (Example 5-c) | 90 (Comparative Example 1-c) | |

TABLE 2

| Sodium ion content (unit: ppb) | Example 1 | Example 2 | Example 3 | Example 4 |
|---|---|---|---|---|
| First step: sulfination | 5150 (Example 1-b) | 4500 (Example 2-a) | | 5020 (Example 4-a) |
| Second step: oxidation | 1580 (Example 1-c) | 1170 (Example 2-b) | 420 (Example 3) | 360 (Example 4-b) |
| Third step: onium ion exchange | 440 (Example 1-d) | | | 220 (Example 4-c) |

| Sodium ion content (unit: ppb) | Example 5 | Comparative Example 1 | Comparative Example 2 |
|---|---|---|---|
| First step: sulfination | 4930 (Example 5-a) | >10000000 (Comparative Example 1-a) | >10000000 (Comparative Example 2-a) |
| Second step: oxidation | 380 (Example 5-b) | >10000000 (Comparative Example 1-b) | >10000000 (Comparative Example 2-b) |
| Third step: onium ion exchange | 200 (Example 5-c) | 3180 (Comparative Example 1-c) | |

As described above, it is possible according to the present invention that the alkoxycarbonylfluoroalkanesulfonic acid salt, which is useful as a photoacid generator, or an intermediate thereof, of a chemically amplified resist material suitably applicable for fine processing, notably photolithography, in the manufacturing of semiconductor devices, can be obtained with high yield by simple operation process under moderate conditions.

Although the present invention has been described with reference to the above specific embodiments, the present invention is not limited to these specific embodiments. Various modifications and variations of the embodiments described above will occur to those skilled in the art without departing from the scope of the present invention.

The invention claimed is:

1. A method for producing an alkoxycarbonylfluoroalkanesulfonic acid salt, comprising the following steps:
   (1) reacting a halofluoroalkanoic acid ester of the general formula [2] with a sulfinating agent in the presence of tert-butylamine or tert-butylammonium chloride to form an alkoxycarbonylfluoroalkanesulfinic acid ammonium salt of the general formula [3];
   (2) purifying the alkoxycarbonylfluoroalkanesulfinic acid ammonium salt by extracting with an organic solvent a crude product of the alkoxycarbonylfluoroalkanesulfinic acid ammonium salt, and then, washing a layer of the organic solvent with either one of water, an aqueous metal thiosulfate solution, and an aqueous metal sulfite solution;

(3) reacting the alkoxycarbonylfluoroalkanesulfinic acid ammonium salt of the general formula [3] with an oxidizing agent, thereby obtaining an alkoxycarbonylfluoroalkanesulfonic acid ammonium salt of the general formula [1];

(4) purifying the alkoxycarbonylfluoroalkanesulfonic acid ammonium salt by recrystallization with an organic solvent; and (5) performing a salt exchange reaction of the alkoxycarbonylfluoroalkanesulfonic acid ammonium salt of the general formula [1] with a monovalent onium salt of the general formula [5], thereby obtaining an alkoxycarbonylfluoroalkanesulfonic acid onium salt of the general formula [4] as the alkoxycarbonylfluoroalkanesulfonic acid salt,

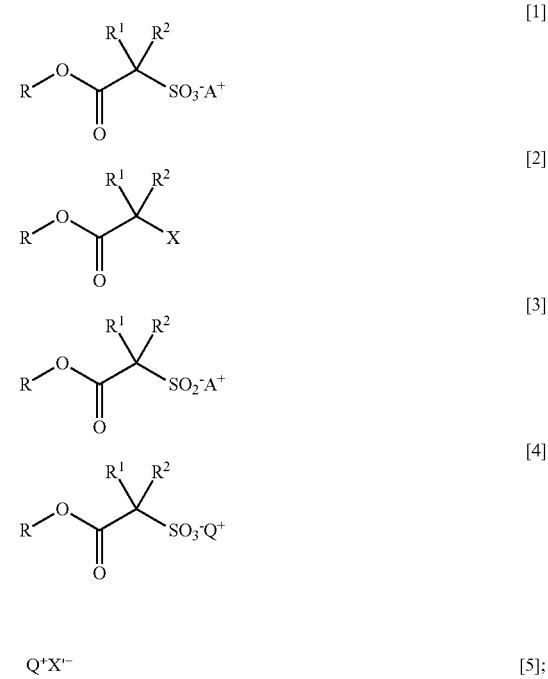

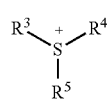

wherein, in the general formula [1], R represents a $C_1$-$C_{10}$ straight or branched alkyl group, a $C_1$-$C_{10}$ straight or branched alkenyl group having at least at an end thereof a polymerizable double bond, a $C_3$-$C_{20}$ alicyclic organic group, an organic group formed of a $C_3$-$C_{20}$ alicyclic organic group and a straight alkylene group, a $C_3$-$C_{30}$ monocyclic or polycyclic lactone group, or a $C_6$-$C_{20}$ aryl group; a part or all of hydrogen atoms of the alkyl group, the alkenyl group, the alicyclic organic group, the organic group formed of the alicyclic organic group and the straight alkylene group, the monocyclic or polycyclic lactone group and the aryl group may be substituted with a fluorine atom, a hydroxyl group, a hydroxycarbonyl group or a $C_1$-$C_6$ straight, branched or cyclic alkoxy group; two hydrogen atoms on the same carbon atom of the alkyl group, the alkenyl group, the alicyclic organic group or the organic group formed of the alicyclic organic group and the straight alkylene group may be replaced with a single oxygen atom to form a keto group; and one of hydrogen atoms of the alkyl group may be substituted with a 2-acryloyloxy group, 2-methacryloyloxy group or 2-trifluoromethacryloyloxy group; $R^1$ and $R^2$ each independently represent a fluorine atom or a $C_1$-$C_6$ straight, branched or cyclic perfluoroalkyl group; and $A^+$ represents tert-butylammonium ion;

wherein, in the general formula [2], X represents a chlorine atom, a bromine atom or an iodine atom; and R, $R^1$ and $R^2$ have the same definitions as in the general formula [1];

wherein, in the general formula [3], R, $R^1$, $R^2$ and $A^+$ have the same definitions as in the general formula [1]

wherein, in the general formula [4], R, $R^1$ and $R^2$ have the same definitions as in the general formula [1]; and $Q^+$ represents a sulfonium cation of the following general formula (a) or the following general formula (b) or an iodonium cation of the following general formula (c); and wherein, in the general formula [5], X' represent a monovalent anion $$R^3\underset{\underset{R^5}{|}}{\overset{+}{S}}R^4 \quad (a)$$

wherein, in the general formula (a), $R^3$, $R^4$ and $R^5$ each independently represent a substituted or unsubstituted $C_1$-$C_{10}$ straight or branched alkyl, alkenyl or oxoalkyl group, or a substituted or unsubstituted $C_6$-$C_{18}$ aryl, aralkyl or aryloxoalkyl group; and two or more of $R^3$, $R^4$ and $R^5$ may be bonded to each other to form a ring with a sulfur atom in the formula;

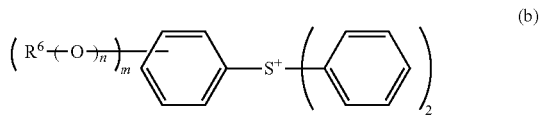

wherein, in the general formula (b), $R^6$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; and n represents 0 or 1;

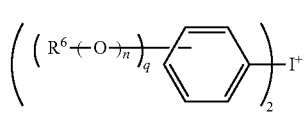

wherein, in the general formula (c), $R^6$ represents a substituted or unsubstituted $C_1$-$C_{20}$ straight, branched or cyclic alkyl or alkenyl group, or a substituted or unsubstituted $C_6$-$C_{14}$ aryl group; q represents an integer of 0 to 5; and n represents 0 or 1;

wherein the sulfinating agent is sodium dithionite.

2. The method according to claim 1, wherein, in the formulas (1) to (4), R is adamantane-1-ylmethyl.

3. The method according to claim 1, wherein the organic solvent used in step (2) is either chloroform or dichloromethane.

4. The method according to claim 1, wherein the organic solvent used in step (4) is a mixed solvent of chloroform, ethyl acetate and diisopropyl ether.

5. The method according to claim 1, wherein the tert-butylamine or tert-butylammonium chloride is used at a mole ratio of 1.0 to 10.0 relative to the halofluoroalkanoic acid ester.

6. The method according to claim 1, further comprising a step (6): purifying the alkoxycarbonylfluoroalkanesulfonic acid onium salt by recrystallization with an organic solvent.

* * * * *